US008506645B2

(12) United States Patent  
Blaylock et al.

(10) Patent No.: US 8,506,645 B2
(45) Date of Patent: Aug. 13, 2013

(54) TIBIAL AUGMENTS FOR USE WITH KNEE JOINT PROSTHESES

(75) Inventors: Jeff Blaylock, Fort Wayne, IN (US); Michael Cook, Claypool, IN (US); Ron Donkers, Warsaw, IN (US); Scott E. Dykema, Warsaw, IN (US); David Jones, Elkhart, IN (US); John E. Meyers, Columbia City, IN (US); Stephen J. Vankoski, Fort Wayne, IN (US); Arlen D. Hanssen, Rochester, MN (US); David G. Lewallen, Rochester, MN (US)

(73) Assignee: Zimmer, Inc., Warsaw, IN (US)

( * ) Notice: Subject to any disclaimer, the term of this patent is extended or adjusted under 35 U.S.C. 154(b) by 74 days.

(21) Appl. No.: 12/886,297

(22) Filed: Sep. 20, 2010

(65) Prior Publication Data

US 2011/0009974 A1   Jan. 13, 2011

Related U.S. Application Data

(63) Continuation of application No. 10/780,378, filed on Feb. 17, 2004, now abandoned, which is a continuation-in-part of application No. 10/225,774, filed on Aug. 22, 2002, now abandoned.

(60) Provisional application No. 60/315,148, filed on Aug. 27, 2001.

(51) Int. Cl.
*A61F 2/32* (2006.01)

(52) U.S. Cl.
USPC ...................................................... 623/23.22

(58) Field of Classification Search
USPC ................................ 623/23.21, 23.22, 20.34
See application file for complete search history.

(56) References Cited

U.S. PATENT DOCUMENTS

| 2,947,308 A | 8/1960 | Gorman |
| 3,658,056 A | 4/1972 | Huggler et al. |

(Continued)

FOREIGN PATENT DOCUMENTS

| AU | 2004203348 A1 | 9/2005 |
| AU | 2004203348 A1 | 9/2005 |

(Continued)

OTHER PUBLICATIONS

Restriction Requirement mailed Aug. 25, 2006 in parent U.S. Appl. No. 10/780,378.

(Continued)

*Primary Examiner* — Paul Prebilic
(74) *Attorney, Agent, or Firm* — Schwegman, Lundberg & Woessner P.A.

(57) ABSTRACT

A tibial augment for use with a knee joint prosthesis, composed of annular members of different stock sizes, each size being configured to fit within a cavity formed in a human tibia. The augment may include a stepped distal surface. A provisional (temporary) tibial augment used to ensure a proper fit for the permanent augment is also provided. The provisional may include grooves configured to cooperate with a set of ribs on a tong-like holder used for removing the provisional from the cavity. A pusher for use implanting the tibial augment is also provided. In addition, a system for creating a cavity in a human tibia is also described. The system preferably includes a guide with a slot therein and a set of osteotomes that are inserted within different portions of the slot. Methods for using the tools and/or implanting the prosthetic devices discussed above are also described.

34 Claims, 12 Drawing Sheets

(56) References Cited

U.S. PATENT DOCUMENTS

| | | | |
|---|---|---|---|
| D230,429 S | 2/1974 | Davidson et al. |
| 3,855,638 A | 12/1974 | Pilliar |
| 3,871,031 A | 3/1975 | Boutin |
| 3,891,997 A | 7/1975 | Herbert |
| 3,903,549 A | 9/1975 | Deyerle |
| 3,918,102 A | 11/1975 | Eichler |
| 4,064,567 A | 12/1977 | Burstein et al. |
| 4,136,405 A | 1/1979 | Pastrick et al. |
| 4,164,794 A | 8/1979 | Spector et al. |
| 4,206,516 A | 6/1980 | Pilliar |
| 4,216,549 A | 8/1980 | Hillberry et al. |
| 4,219,893 A | 9/1980 | Noiles |
| 4,224,696 A | 9/1980 | Murray et al. |
| 4,404,691 A | 9/1983 | Buning et al. |
| 4,444,061 A | 4/1984 | Mathias |
| 4,523,587 A | 6/1985 | Frey |
| 4,549,319 A | 10/1985 | Meyer |
| 4,659,331 A | 4/1987 | Matthews et al. |
| 4,662,891 A | 5/1987 | Noiles |
| 4,678,470 A | 7/1987 | Nashef et al. |
| 4,711,639 A | 12/1987 | Grundei |
| 4,718,909 A | 1/1988 | Brown |
| 4,735,625 A | 4/1988 | Davidson |
| 4,778,473 A | 10/1988 | Matthews et al. |
| 4,789,663 A | 12/1988 | Wallace et al. |
| 4,790,852 A | 12/1988 | Noiles |
| 4,822,366 A | 4/1989 | Bolesky |
| 4,827,919 A | 5/1989 | Barbarito et al. |
| 4,828,565 A | 5/1989 | Duthoit et al. |
| 4,834,759 A | 5/1989 | Spotorno et al. |
| 4,878,919 A | 11/1989 | Pavlansky et al. |
| 4,883,448 A | 11/1989 | Kobayashi et al. |
| 4,883,488 A | 11/1989 | Bloebaum et al. |
| 4,888,021 A | 12/1989 | Forte et al. |
| 4,944,757 A | 7/1990 | Martinez et al. |
| 4,950,298 A | 8/1990 | Gustilo et al. |
| 4,988,359 A | 1/1991 | Frey et al. |
| 5,019,103 A | 5/1991 | Van Zile et al. |
| 5,032,134 A | 7/1991 | Lindwer |
| 5,059,196 A | 10/1991 | Coates |
| 5,092,897 A | 3/1992 | Forte |
| 5,108,446 A | 4/1992 | Wagner et al. |
| 5,133,771 A | 7/1992 | Duncan et al. |
| 5,152,797 A | 10/1992 | Luckman et al. |
| 5,156,626 A | 10/1992 | Broderick et al. |
| 5,163,966 A | 11/1992 | Norton et al. |
| 5,176,711 A | 1/1993 | Grimes |
| 5,197,488 A | 3/1993 | Kovacevic |
| 5,211,664 A | 5/1993 | Tepic et al. |
| 5,222,984 A | 6/1993 | Forte |
| 5,226,915 A | 7/1993 | Bertin |
| 5,246,459 A | 9/1993 | Elias |
| 5,356,414 A | 10/1994 | Cohen et al. |
| 5,356,629 A | 10/1994 | Sander et al. |
| 5,358,527 A | 10/1994 | Forte |
| 5,358,530 A | 10/1994 | Hodorek |
| 5,370,693 A | 12/1994 | Kelman et al. |
| 5,376,123 A | 12/1994 | Klaue et al. |
| 5,387,241 A | 2/1995 | Hayes |
| 5,405,394 A | 4/1995 | Davidson |
| 5,413,604 A | 5/1995 | Hodge |
| 5,462,563 A | 10/1995 | Shearer et al. |
| 5,480,445 A | 1/1996 | Burkinshaw |
| 5,489,311 A * | 2/1996 | Cipolletti ................... 623/20.34 |
| 5,507,830 A | 4/1996 | DeMane et al. |
| 5,510,396 A | 4/1996 | Prewett et al. |
| 5,531,791 A | 7/1996 | Wolfinbarger, Jr. |
| 5,549,685 A | 8/1996 | Hayes |
| 5,571,198 A | 11/1996 | Drucker et al. |
| 5,591,233 A | 1/1997 | Kelman et al. |
| 5,609,645 A * | 3/1997 | Vinciguerra ............... 623/20.28 |
| 5,658,338 A | 8/1997 | Tullos et al. |
| 5,658,349 A | 8/1997 | Brooks et al. |
| 5,662,158 A | 9/1997 | Caldarise |
| 5,683,467 A | 11/1997 | Pappas |
| 5,702,478 A | 12/1997 | Tornier |
| 5,702,483 A | 12/1997 | Kwong |
| 5,734,959 A | 3/1998 | Krebs et al. |
| 5,766,256 A | 6/1998 | Oudard et al. |
| 5,782,925 A | 7/1998 | Collazo et al. |
| 5,782,929 A | 7/1998 | Sederholm |
| 5,788,976 A | 8/1998 | Bradford |
| 5,824,103 A | 10/1998 | Williams |
| 5,858,020 A | 1/1999 | Johnson et al. |
| 5,871,548 A | 2/1999 | Sanders et al. |
| 5,879,393 A | 3/1999 | Whiteside et al. |
| 5,910,172 A | 6/1999 | Penenberg |
| 5,931,409 A | 8/1999 | Nulle et al. |
| 5,957,979 A | 9/1999 | Beckman et al. |
| 5,958,314 A * | 9/1999 | Draenert ........................ 264/42 |
| 5,972,368 A | 10/1999 | McKay |
| 5,976,148 A | 11/1999 | Charpenet et al. |
| 5,984,968 A | 11/1999 | Park |
| 5,993,716 A * | 11/1999 | Draenert ..................... 264/221 |
| 5,997,581 A | 12/1999 | Khalili |
| 6,008,432 A | 12/1999 | Taylor |
| 6,013,080 A | 1/2000 | Khalili |
| 6,039,764 A | 3/2000 | Pottenger et al. |
| 6,042,612 A | 3/2000 | Voydeville |
| 6,053,945 A | 4/2000 | O'Neil et al. |
| 6,074,423 A | 6/2000 | Lawson |
| 6,074,424 A | 6/2000 | Perrone, Jr. et al. |
| 6,080,195 A | 6/2000 | Colleran et al. |
| 6,117,175 A | 9/2000 | Bosredon |
| 6,126,691 A | 10/2000 | Kasra et al. |
| 6,136,029 A | 10/2000 | Johnson et al. |
| 6,139,581 A | 10/2000 | Engh et al. |
| 6,139,584 A | 10/2000 | Ochoa et al. |
| 6,142,998 A | 11/2000 | Smith et al. |
| 6,162,254 A | 12/2000 | Timoteo |
| 6,162,255 A * | 12/2000 | Oyola ....................... 623/20.34 |
| 6,171,342 B1 | 1/2001 | O'Neil et al. |
| 6,264,699 B1 | 7/2001 | Noiles et al. |
| 6,290,725 B1 | 9/2001 | Weiss et al. |
| 6,328,764 B1 | 12/2001 | Mady |
| 6,355,069 B1 * | 3/2002 | DeCarlo et al. ............ 623/23.26 |
| 6,368,352 B1 | 4/2002 | Camino et al. |
| 6,423,096 B1 | 7/2002 | Musset et al. |
| 6,428,578 B2 | 8/2002 | White |
| 6,447,549 B1 | 9/2002 | Taft |
| 6,458,161 B1 | 10/2002 | Gibbs et al. |
| 6,613,092 B1 | 9/2003 | Kana et al. |
| 6,699,293 B2 | 3/2004 | White |
| 6,797,006 B2 | 9/2004 | Hodorek |
| 6,843,806 B2 | 1/2005 | Hayes et al. |
| 6,875,218 B2 | 4/2005 | Dye et al. |
| 6,875,237 B2 | 4/2005 | Dye et al. |
| 6,926,740 B2 | 8/2005 | Lewis et al. |
| 6,946,001 B2 | 9/2005 | Sanford et al. |
| 6,981,991 B2 | 1/2006 | Ferree |
| 7,105,026 B2 | 9/2006 | Johnson et al. |
| 7,179,295 B2 | 2/2007 | Kovacevic |
| 7,179,296 B2 | 2/2007 | Dooney |
| 7,179,297 B2 | 2/2007 | McLean |
| 7,179,298 B2 | 2/2007 | Greenlee |
| D538,431 S | 3/2007 | Botha |
| 7,238,208 B2 | 7/2007 | Camino et al. |
| 7,264,636 B2 | 9/2007 | Lewis et al. |
| 7,291,174 B2 | 11/2007 | German et al. |
| 7,291,177 B2 | 11/2007 | Gibbs |
| 7,435,263 B2 | 10/2008 | Barnett et al. |
| 7,713,306 B2 | 5/2010 | Gibbs |
| D618,800 S | 6/2010 | Mayon et al. |
| 7,846,212 B2 | 12/2010 | Lewis et al. |
| 7,892,288 B2 | 2/2011 | Blaylock et al. |
| 7,892,289 B2 | 2/2011 | Serafin, Jr. et al. |
| 8,123,814 B2 | 2/2012 | Meridew et al. |
| 8,382,849 B2 * | 2/2013 | Thomas ..................... 623/20.34 |
| 2002/0151984 A1* | 10/2002 | White ........................ 623/23.22 |
| 2003/0065397 A1 | 4/2003 | Hanssen et al. |
| 2003/0153981 A1* | 8/2003 | Wang et al. ................. 623/22.21 |
| 2003/0163203 A1 | 8/2003 | Nycz et al. |
| 2003/0183025 A1 | 10/2003 | Krstic |
| 2003/0229398 A1 | 12/2003 | Iesaka |

| | | | |
|---|---|---|---|
| 2004/0034432 | A1 | 2/2004 | Hughes et al. |
| 2004/0049270 | A1* | 3/2004 | Gewirtz ..................... 623/17.11 |
| 2004/0049284 | A1 | 3/2004 | German et al. |
| 2004/0117024 | A1 | 6/2004 | Gerbec et al. |
| 2004/0162619 | A1 | 8/2004 | Blaylock et al. |
| 2004/0172137 | A1 | 9/2004 | Blaylock et al. |
| 2005/0107883 | A1 | 5/2005 | Goodfried et al. |
| 2005/0278034 | A1 | 12/2005 | Johnson et al. |
| 2005/0283254 | A1 | 12/2005 | Hayes et al. |
| 2007/0088443 | A1* | 4/2007 | Hanssen et al. ............ 623/23.46 |
| 2007/0129809 | A1 | 6/2007 | Meridew et al. |
| 2008/0167722 | A1 | 7/2008 | Metzger et al. |
| 2008/0281430 | A1 | 11/2008 | Kelman et al. |
| 2010/0145452 | A1 | 6/2010 | Blaylock et al. |
| 2011/0066252 | A1 | 3/2011 | Hanssen et al. |
| 2011/0112651 | A1 | 5/2011 | Blaylock et al. |
| 2011/0295382 | A1 | 12/2011 | Hanssen et al. |
| 2013/0013078 | A1 | 1/2013 | Hanssen et al. |
| 2013/0013080 | A1 | 1/2013 | Hanssen et al. |
| 2013/0018478 | A1 | 1/2013 | Hanssen et al. |

FOREIGN PATENT DOCUMENTS

| | | |
|---|---|---|
| CA | 2473633 A1 | 9/2005 |
| CA | 2473633 A1 | 9/2005 |
| EP | 0336774 B1 | 12/1992 |
| EP | 0532585 B1 | 4/2000 |
| EP | 1004283 A2 | 5/2000 |
| EP | 1004283 A2 | 5/2000 |
| EP | 0863731 B1 | 4/2001 |
| EP | 1004283 A3 | 3/2002 |
| EP | 1004283 B1 | 5/2005 |
| FR | 2772593 A1 | 6/1999 |
| FR | 2772593 A1 | 6/1999 |
| GB | 2223172 A | 4/1990 |
| GB | 2223172 A | 4/1990 |
| JP | 6-169930 A | 6/1994 |
| JP | 6169930 A | 6/1994 |
| JP | 10-277069 A | 10/1998 |
| JP | 10277069 A | 10/1998 |
| JP | 2000-185062 A | 7/2000 |
| JP | 2000185062 A | 7/2000 |
| JP | 2001-503283 T | 3/2001 |
| JP | 2001503283 A | 3/2001 |
| JP | 2001-526573 T | 12/2001 |
| JP | 2001526573 A | 12/2001 |
| JP | 2004-016822 A | 1/2004 |
| JP | 2004016822 A | 1/2004 |
| JP | 2005-246036 A | 9/2005 |
| JP | 2005246036 A | 9/2005 |
| WO | WO97/30661 A1 | 8/1997 |
| WO | WO-9730661 A1 | 8/1997 |
| WO | WO-9932053 A1 | 7/1999 |
| WO | WO02/05732 A1 | 1/2002 |
| WO | WO-0205732 A1 | 1/2002 |
| WO | WO-2009089581 A1 | 7/2009 |

OTHER PUBLICATIONS

Election filed Sep. 15, 2006 in parent U.S. Appl. No. 10/780,378.
Restriction Requirement mailed Dec. 4, 2006 in parent U.S. Appl. No. 10/780,378.
Election filed Jan. 4, 2007 in parent U.S. Appl. No. 10/780,378.
Office Action mailed Mar. 30, 2007 in parent U.S. Appl. No. 10/780,378.
Amendment filed Jun. 15, 2007 in parent U.S. Appl. No. 10/780,378.
Final Office Action mailed Aug. 27, 2007 in parent U.S. Appl. No. 10/780,378.
Amendment filed Oct. 31, 2007 in parent U.S. Appl. No. 10/780,378.
Office Action mailed Dec. 12, 2007 in parent U.S. Appl. No. 10/780,378.
Amendment filed May 28, 2008 in parent U.S. Appl. No. 10/780,378.
Final Office Action mailed Aug. 21, 2008 in parent U.S. Appl. No. 10/780,378.
Amendment filed Nov. 12, 2008 in parent U.S. Appl. No. 10/780,378.
Office Action mailed Feb. 2, 2009 in parent U.S. Appl. No. 10/780,378.
Amendment filed Jun. 24, 2009 in parent U.S. Appl. No. 10/780,378.
Restriction Requirement mailed Oct. 22, 2009 in parent U.S. Appl. No. 10/780,378.
Election filed Dec. 22, 2009 in parent U.S. Appl. No. 10/780,378.
Final Office Action mailed Apr. 20, 2010 in parent U.S. Appl. No. 10/780,378.
Office Action mailed Nov. 2, 2006 in related US Appl. No. 10/794,721.
Office Action mailed Aug. 3, 2007 in related U.S. Appl. No. 10/794,721.
Final Office Action mailed Jan. 16, 2008 in related U.S. Appl. No. 10/794,721.
Office Action mailed Jul. 8, 2008 in related U.S. Appl. No. 10/794,721.
Final Office Action mailed Jan. 1, 2009 in related U.S. Appl. No. 10/794,721.
Office Action mailed Jun. 15, 2009 in related U.S. Appl. No. 10/794,721.
US 5,536,414, 10/1994, Cohen et al. (withdrawn).
U.S. Appl. No. 10/780,378, Final Office Action mailed Apr. 20, 2010, 7 pgs.
U.S. Appl. No. 10/780,378, Final Office Action mailed Aug. 21, 2008, 6 pgs.
U.S. Appl. No. 10/780,378, Final Office Action mailed Aug. 27, 2007, 7 pgs.
U.S. Appl. No. 10/780,378, Non-Final Office Action mailed Feb. 2, 2009, 7 pgs.
U.S. Appl. No. 10/780,378, Non-Final Office Action mailed Mar. 30, 2007, 7 pgs.
U.S. Appl. No. 10/780,378, Non-Final Office Action mailed Dec. 12, 2007, 8 pgs.
U.S. Appl. No. 10/780,378, Preliminary Amendment filed Jun. 1, 2004, 20 pgs.
U.S. Appl. No. 10/780,378, Response filed Jan. 8, 2007 to Restriction Requirement mailed Dec. 4, 2006, 1 pg.
U.S. Appl. No. 10/780,378, Response filed May 28, 2008 to Non-Final Office Action mailed Dec. 12, 2007, 11 pgs.
U.S. Appl. No. 10/780,378, Response filed Jun. 15, 2007 to Non-Final Office Action mailed Mar. 30, 2007, 7 pgs.
U.S. Appl. No. 10/780,378, Response filed Jun. 24, 2009 to Non-Final Office Action mailed Feb. 2, 2009, 15 pgs.
U.S. Appl. No. 10/780,378, Response filed Sep. 19, 2006 to Restriction Requirement mailed Aug. 25, 2006, 1 pg.
U.S. Appl. No. 10/780,378, Response filed Oct. 31, 2007 to Final Office Action mailed Aug. 27, 2007, 8 pgs.
U.S. Appl. No. 10/780,378, Response filed Nov. 12, 2008 to Final Office Action mailed Aug. 21, 2008, 10 pgs.
U.S. Appl. No. 10/780,378, Response filed Dec. 22, 2009 Restriction Requirement mailed Oct. 22, 2009, 2 pgs.
U.S. Appl. No. 10/780,378, Restriction Requirement mailed Aug. 25, 2006, 6 pgs.
U.S. Appl. No. 10/780,378, Restriction Requirement mailed Oct. 22, 2009, 7 pgs.
U.S. Appl. No. 10/780,378, Restriction Requirement mailed Dec. 4, 2006, 6 pgs.
U.S. Appl. No. 10/794,721, Final Office Action mailed May 6, 2010, 8 pgs.
U.S. Appl. No. 10/794,721, Final Office Action mailed Jan. 16, 2008, 8 pgs.
U.S. Appl. No. 10/794,721, Final Office Action mailed Jan. 16, 2009, 6 pgs.
U.S. Appl. No. 10/794,721, Non Final Office Action mailed Aug. 3, 2007, 7 pgs.
U.S. Appl. No. 10/794,721, Non-Final Office Action mailed Jun. 15, 2009, 9 pgs.
U.S. Appl. No. 10/794,721, Notice of Allowance mailed Oct. 14, 2010, 6 pgs.
U.S. Appl. No. 10/794,721, Office Action mailed Jul. 8, 2008, 6 pgs.
U.S. Appl. No. 10/794,721, Office Action mailed Nov. 2, 2006, 7 pgs.
U.S. Appl. No. 10/794,721, Response filed Feb. 2, 2007 to Non Final Office Action mailed Nov. 2, 2006, 7 pgs.
U.S. Appl. No. 10/794,721, Response filed Feb. 8, 2010 to Non Final Office Action mailed Jan. 12, 2010, 2 pgs.

U.S. Appl. No. 10/794,721, Response filed May 18, 2007 to Non Final Office Action mailed Nov. 2, 2006, 7 pgs.
U.S. Appl. No. 10/794,721, Response filed Sep. 28, 2009 to Non Final Office Action mailed Jun. 15, 2009, 10 pgs.
U.S. Appl. No. 10/794,721, Response filed Oct. 6, 2010 to Final Office Action mailed May 6, 2010, 6 pgs.
U.S. Appl. No. 10/794,721, Response filed Oct. 8, 2008 to Non Final Office Action mailed Jul. 8, 2008, 8 pgs.
U.S. Appl. No. 10/794,721, Response filed Nov. 8, 2007 to Non Final Office Action mailed Aug. 3, 2007, 7 pgs.
U.S. Appl. No. 11/560,276, Final Office Action mailed Oct. 8, 2010, 6 pgs.
U.S. Appl. No. 11/560,276, Non Final Office Action mailed Mar. 3, 2010, 8 pgs.
U.S. Appl. No. 11/560,276, Non Final Office Action mailed Aug. 11, 2011, 6 pgs.
U.S. Appl. No. 11/560,276, Response filed Feb. 7, 2011 to Final Office Action mailed Oct. 8, 2010, 10 pgs.
U.S. Appl. No. 11/560,276, Response filed Feb. 13, 2012 to Non Final Office Action mailed Aug. 11, 2011, 13 pgs.
U.S. Appl. No. 11/560,276, Response filed Aug. 2, 2010 to Non Final Office Action mailed Mar. 3, 2010, 12 pgs.
U.S. Appl. No. 11/560,276, Response filed Oct. 21, 2009 to Restriction Requirement mailed Aug. 21, 2009, 12 pgs.
U.S. Appl. No. 11/560,276, Restriction Requirement mailed Aug. 21, 2009, 7 pgs.
U.S. Appl. No. 12/946,132, Examiner Interview Summary mailed Jun. 5, 2012, 3 pgs.
U.S. Appl. No. 12/946,132, Final Office Action mailed Jul. 25, 2012, 12 pgs.
U.S. Appl. No. 12/946,132, Non Final Office Action mailed Mar. 28, 2012, 10 pgs.
U.S. Appl. No. 12/946,132, Response filed Jun. 27, 2012 to non Final Office Action mailed Mar. 28, 2012, 15 pgs.
U.S. Appl. No. 12/946,132, Response filed Sep. 6, 2011 to Restriction Requirement mailed Aug. 23, 2011, 8 pgs.
U.S. Appl. No. 12/946,132, Response filed Sep. 24, 2012 to Final Office Action mailed Jul. 25, 2012, 16 pgs.
U.S. Appl. No. 12/946,132, Restriction Requirement mailed Aug. 23, 2011, 8 pgs.
U.S. Appl. No. 13/007,225, Preliminary Amendment filed Jan. 14, 2011, 4 pgs.
U.S. Appl. No. 13/007,225, Restriction Requirement mailed Sep. 20, 2012, 8 pgs.
U.S. Appl. No. 13/007,225, Supplemental Preliminary Amendment filed Sep. 23, 2011, 8 pgs.
U.S. Appl. No. 29/379,094, filed Nov. 15, 2010, 6 pgs.
U.S. Appl. No. 29/379,094, Restriction Requirement mailed Oct. 23, 2012, 7 pgs.
Australian Application No. 2004203348, Office Action mailed Jan. 13, 2010, 3 pgs.
Canadian Application No. 2,473,633, Office Action mailed Mar. 12, 2010, 3 pgs.
European Application No. 04254352.0 European Search Report mailed Jun. 22, 2005, 3 pgs.
Japanese Application No. 2004-216179, Office Action mailed May 26, 2009, 8 pgs.
"U.S. Appl. No. 10/225,774, Advisory Action mailed Oct. 26, 2005", 3 pgs.
"U.S. Appl. No. 10/225,774, Examiner Interview Summary Mar. 17, 2005", 4 pgs.
"U.S. Appl. No. 10/225,774, Final Office Action mailed Jun. 6, 2005", 9 pgs.
"U.S. Appl. No. 10/225,774, Final Office Action mailed Aug. 17, 2006", 8 pgs.
"U.S. Appl. No. 10/225,774, Non-Final Office Action mailed Feb. 8, 2006", 6 pgs.
"U.S. Appl. No. 10/225,774, Non-Final Office Action mailed Jun. 30, 2004", 5 pgs.
"U.S. Appl. No. 10/225,774, Non-Final Office Action mailed Dec. 8, 2004", 6 pgs.
"U.S. Appl. No. 10/225,774, Response filed Mar. 7, 2005 to Non-Final Office Action mailed Dec. 8, 2004", 21 pgs.
"U.S. Appl. No. 10/225,774, Response filed Apr. 16, 2004 to Restriction Requirement mailed Mar. 17, 2004", 1 pg.
"U.S. Appl. No. 10/225,774, Response filed Jun. 7, 2006 to Non-Final Office Action mailed Feb. 8, 2006", 21 pgs.
"U.S. Appl. No. 10/225,774, Response filed Sep. 20, 2004 to Non-Final Office Action mailed Jun. 30, 2004", 14 pgs.
"U.S. Appl. No. 10/225,774, Response filed Oct. 6, 2005 to Final Office Action mailed Jun. 6, 2005", 21 pgs.
"U.S. Appl. No. 10/225,774, Response filed Nov. 15, 2006 to Final Office Action mailed Aug. 17, 2006", 1 pg.
"U.S. Appl. No. 10/225,774, Restriction Requirement mailed Mar. 17, 2004", 6 pgs.
"U.S. Appl. No. 10/794,721, Response filed Apr. 14, 2009 to Final Office Action mailed Jan. 16, 2009", 8 pgs.
"U.S. Appl. No. 10/794,721, Response filed Jun. 16, 2008 to Final Office Action mailed Jan. 16, 2008", 8 pgs.
"U.S. Appl. No. 11/560,276, Examiner Interview Summary mailed Jan. 18, 2012", 4 pgs.
"U.S. Appl. No. 11/560,276, Examiner Interview Summary mailed Jun. 5, 2012", 3 pgs.
"U.S. Appl. No. 11/560,276, Final Office Action mailed Mar. 27, 2012", 8 pgs.
"U.S. Appl. No. 11/560,276, Response filed Jun. 27, 2012 to Final Office Action mailed Mar. 27, 2012", 12 pgs.
"U.S. Appl. No. 13/007,225, Non Final Office Action mailed Nov. 19, 2012", 9 pgs.
"U.S. Appl. No. 13/007,225, Response filed Mar. 12, 2013 to Non-Final Office Action mailed Nov. 19, 2012", 13 pgs.
"U.S. Appl. No. 13/007,225, Response filed Oct. 22, 2012 to Restriction Requirement mailed Sep. 20, 2012", 10 pgs.
"U.S. Appl. No. 13/205,163, Preliminary Amendment filed Aug. 8, 2011", 8 pgs.
"U.S. Appl. No. 13/205,163, Response filed Feb. 21, 2013 to Restriction Requirement mailed Jan. 24, 2013", 10 pgs.
"U.S. Appl. No. 13/205,163, Restriction Requirement mailed Jan. 24, 2013", 6 pgs.
"U.S. Appl. No. 13/619,190, Preliminary Amendment filed Oct. 29, 2012", 8 pgs.
"U.S. Appl. No. 29/379,094, Notice of Allowance mailed Feb. 28, 2013", 12 pgs.
"U.S. Appl. No. 29/379,094, Response filed Nov. 21, 2012 to Restriction Requirement mailed Oct. 23, 2012", 4 pgs.
"U.S. Appl. No. 13/007,225, Examiner Interview Summary mailed May 30, 2013", 23 pgs.
"U.S. Appl. No. 13/007,225, Final Office Action mailed Apr. 18, 2013", 10 pgs.
"U.S. Appl. No. 13/205,163, Non Final Office Action mailed Apr. 4, 2013", 8 pgs.
"U.S. Appl. No. 13/416,857, Non Final Office Action mailed Feb. 25, 2013", 17 pgs.
"U.S. Appl. No. 13/416,857, Response filed May 24, 2013 to Non Final Office Action mailed Feb. 25, 2013", 15 pgs.
"Forbes Magazine Ranks Zimmer Holdings Among the 'Best Managed Companies in America'", PR Newswire, (Jan. 23, 2004), 2 pgs.

* cited by examiner

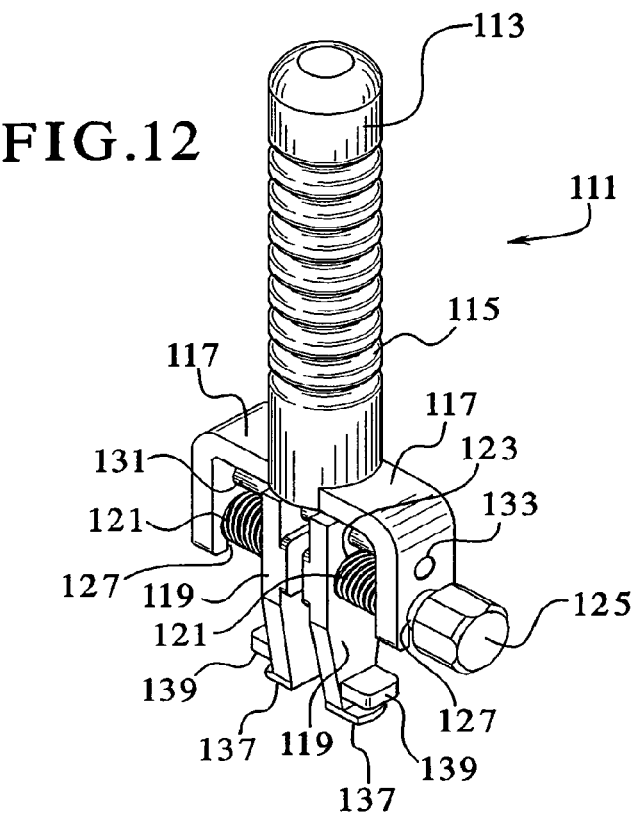
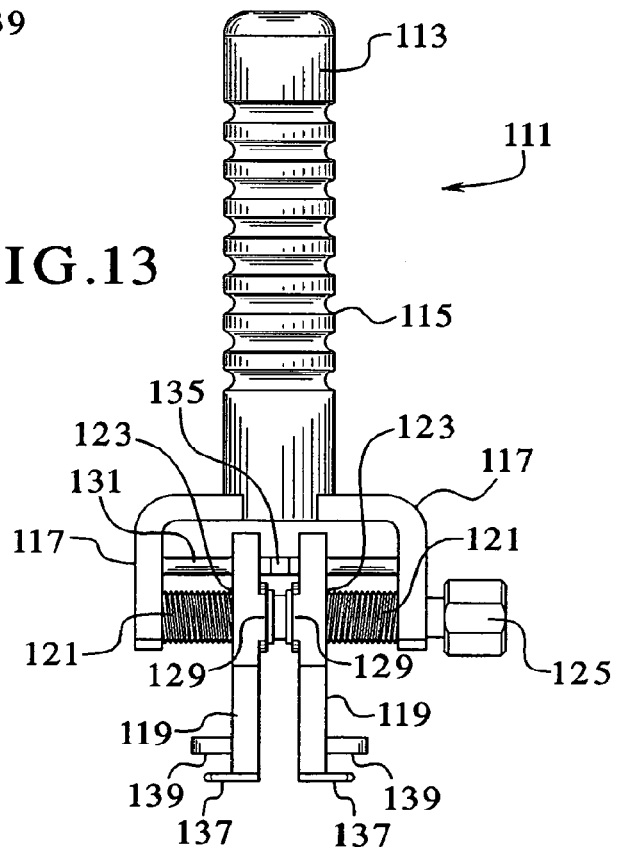

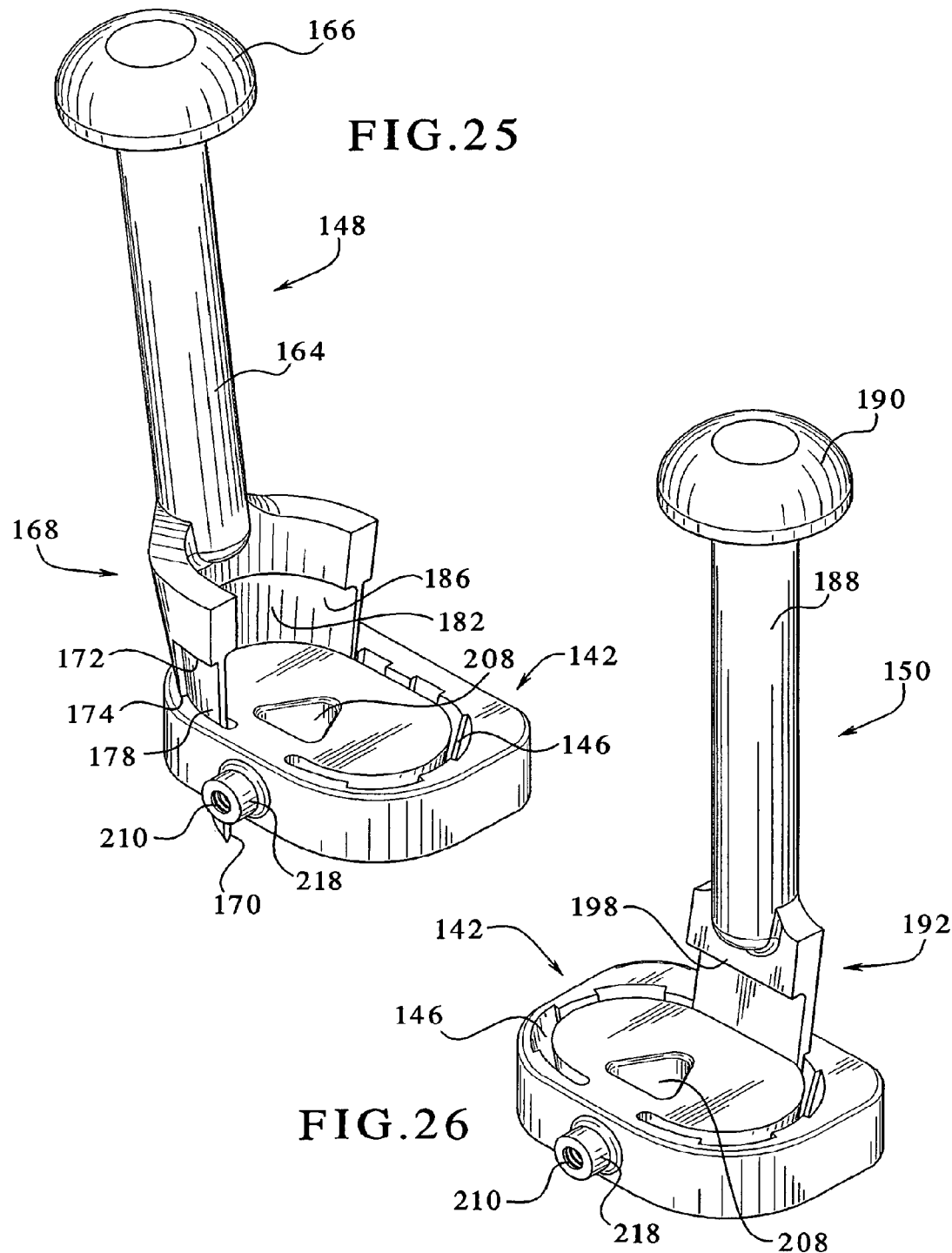

TIBIAL AUGMENTS FOR USE WITH KNEE JOINT PROSTHESES

CROSS REFERENCE TO RELATED APPLICATION

This application is a continuation of U.S. patent application Ser. No. 10/780,378, filed Feb. 17, 2004, entitled "TIBIAL AUGMENTS FOR USE WITH KNEE JOINT PROSTHESES, METHOD OF IMPLANTING THE TIBIAL AUGMENT, AND ASSOCIATED TOOLS" (now abandoned) which is a continuation-in-part of U.S. patent application Ser. No. 10/225,774, filed Aug. 22, 2002, entitled "TIBIAL AUGMENTS FOR USE WITH KNEE JOINT PROSTHESES, METHOD OF IMPLANTING THE TIBIAL AUGMENT, AND ASSOCIATED TOOLS" (now abandoned) which claims the benefit of Provisional Application No. 60/315,148, filed Aug. 27, 2001, the disclosures of which are hereby expressly incorporated by reference herein in its entirety.

The present invention relates generally to a bone augmenting member used to reinforce damaged bone, and more particularly to an augment for the proximal portion of a human tibia, where the augment is intended to be implanted in the proximal portion of the tibia, just slightly below the tibial portion of a knee joint prosthesis. The present invention also relates to the tool used for implanting the tibial augment, and the tools used for making the cavity in the bone to receive the augment. In addition, the invention also relates to a provisional augment used temporarily to ensure that the permanent augment will be seated within the bone correctly, as well as to a holder used for holding, inserting and removing the provisional augment.

BACKGROUND OF THE INVENTION

Knee replacement surgery methods and knee joint prostheses are known in the art. A typical knee joint prosthesis includes a rounded femoral component that is attached to the distal portion of the femur, and a tibial component, which may be formed of a single piece or from two separate pieces that are joined together, that is attached to the proximal portion of the tibia. The femoral component rides on the exposed surface of the tibial component, replicating natural knee movement as closely as possible. When such knee replacement surgery is performed, an incision is made to expose the knee joint in order to enable removal of both the proximal portion of the tibia and the distal portion of the femur, which creates surfaces upon which the tibial and femoral components of the knee prosthesis can be attached.

In certain situations, additional portions of the tibia, other than the relatively narrow proximal portion being removed during knee replacement surgery, may also be damaged by arthritis or other problems. In such situations, a relatively thick proximal portion of the tibia is often removed, and it is replaced with an augment block shaped like the bone that has been removed. However, such previously known methods often result in the removal of an unnecessary amount of healthy bone, along with the damaged bone. Thus, for example, even in cases where the peripheral bone was healthy, and only the internal bone was damaged, prior art methods often removed both the healthy peripheral bone and the damaged internal bone.

BRIEF SUMMARY OF THE INVENTION

The present invention is intended for situations in which the proximal portion of the tibia is defective, and it provides a method and devices that allow for preservation of healthy peripheral bone, while still providing the necessary augmentation to the proximal portion of the tibia. Preservation of the healthy peripheral bone provides for early onset of bony ingrowth into the tibial augment and allows the bone to infiltrate the augment, restoring the bony platform upon which other implants can reside.

More specifically, the present invention provides a tibial augment for use with a knee joint prosthesis that is made of an annular member with a proximal surface, a distal surface, an outer anterior surface, an inner anterior surface, an outer posterior surface, an inner posterior surface, an inner lateral surface, an outer lateral surface, an inner medial surface and an outer medial surface. Preferably, the outer lateral surface is curved to define a continuous surface connecting the outer posterior to surface and the outer anterior surface; and the outer medial surface is also curved to define a continuous surface connecting the outer posterior surface and the outer anterior surface. In addition, the outer anterior surface is slightly curved and the outer posterior surface is a generally planar surface. The annular member can be made in a variety of different stock sizes, with each size being configured to fit within a cavity formed in a proximal portion of a different sized human tibia.

In certain embodiments, the tibial augment of the present invention can include a stepped distal surface, thereby defining a first distal surface and a second distal surface with a transition surface therebetween, where the first distal surface is located at a greater distance from the proximal surface than the second distal surface. The transition surface can be located at different portions of the augment, such as: (1) midway between the outer lateral surface and the outer medial surface; (2) closer to the outer lateral surface than to the outer medial surface; or (3) closer to the outer medial surface than to the outer lateral surface.

The present invention also includes a provisional or temporary tibial augment that is used to ensure a proper fit for the permanent augment. The provisional augment is preferably composed of a material that is substantially transparent to allow visualization of the bony contact surfaces that will likely contact the augment. In addition, in the preferred embodiment, the provisional augment preferably includes at least one set of generally lateral/medial extending grooves to facilitate removal of the provisional from the cavity formed in the tibia. The grooves are configured to cooperate with a set of ribs on a tong-like holder used for inserting and removing the provisional from the cavity.

The present invention also relates to a pusher for use in implanting the tibial augment, where the pusher includes a handle portion and an augment seating portion. The augment seating portion is connected to one end of the handle portion, and is configured and arranged to seat a particularly sized tibial augment.

In addition, the present invention also relates to a system used for creating a cavity in a proximal portion of a human tibia for use prior to implanting a knee joint prosthesis. The system preferably includes a guide with a slot therein and a set of osteotomes that are configured and arranged to be inserted within different portions of the slot on the guide.

Additionally, the present invention also relates to a holder for inserting and/or removing a provisional augment to/from a cavity in a bone. The holder preferably includes a body portion, a pair of legs extending from the body portion, a finger connected to each of the legs, and a rib extending outwardly from each of the fingers. Each of the ribs preferably extends in a direction that is generally perpendicular to the longitudinal axis of the body portion, and the ribs are configured and arranged to correspond to grooves on an inner surface of a provisional augment. In a first preferred embodiment of the holder, the pair of legs comprises a pair of flexible legs, such that application of a force upon outer surfaces of the legs allows for the ribs to be disengaged from the grooves on the inner surface of the provisional augment without significantly altering the location of the provision augment. In the second preferred embodiment of the holder, each of the legs is a relatively rigid member, and each of the fingers is attached to one of the legs such that the fingers are movable with respect to the legs, whereby movement of the fingers with respect to the legs allows for the ribs to be disengaged from the grooves on the inner surface of the provisional augment without significantly altering the location of the provision augment. The second embodiment of the holder is also preferably adjustable to permit a single holder to be used with provisional augments of different sizes.

The present invention also relates to the methods of using the tools and/or implanting the prosthetic devices discussed above.

BRIEF DESCRIPTION OF THE DRAWINGS

Preferred embodiments of the present invention are described herein with reference to the drawings wherein:

FIG. 12 is a perspective view of a second embodiment of a holder of the present invention;

FIG. 13 is a front view of the holder of FIG. 12;

FIG. 25 is a perspective view of the guide of FIG. 18, shown with a second osteotome of the present invention;

FIG. 26 is a perspective view of the guide of FIG. 18, shown with a third osteotome of the present invention;

DETAILED DESCRIPTION OF THE INVENTION

Figure 1:
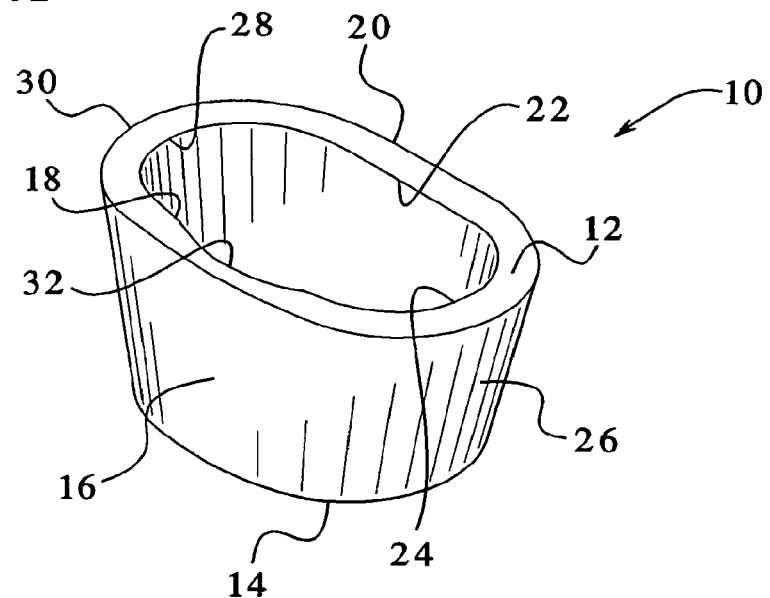
FIG. 1 is a perspective view of a preferred embodiment of a tibial augment of the present invention.

Referring to FIGS. 1 through 4, a first embodiment of the tibial augment of the present invention is shown. The tibial augment is preferably an annular member 10, and it is preferably made from a tantalum based porous material, such as Trabecular Metal™. Trabecular Metal™ is desirable because it resembles bone and approximates the physical and mechanical properties of bone better than other materials. Use of such a metal enables increased bonding with the adjacent bone by allowing the bone to grow into its highly porous surface. The tibial augment may also be made of other materials, and it is preferably made of a material that facilitates bony ingrowth.

The tibial augment 10 is anatomically sized and shaped to fill an existing cavitary defect within the proximal human tibia or a cavity prepared in the proximal portion of a human tibia. In the preferred embodiment, a system of different stock sizes of augments would be available, as discussed more fully below, with different sizes being used for different sized tibias. Further, if desired two augments of different sizes may be stacked upon each other if such stacking is necessary to fill the cavity.

As shown in FIGS. 1 through 4, the tibial augment 10 includes a proximal surface 12, a distal surface 14, an outer anterior surface 16, an inner anterior surface 18, an outer posterior surface 20, an inner posterior surface 22, an inner lateral surface 24, an outer lateral surface 26, an inner medial surface 28 and an outer medial surface 30. Of course, depending on which tibia (right or left) the augment is being implanted into, the surfaces designated as the medial and lateral surfaces will be reversed. However, since the augment is symmetric with respect to its lateral and medial sides, such distinctions are irrelevant, and the terms lateral and medial are being used for convenience of description only.

To mimic the portion of the tibia bone that the tibial augment is being implanted into, the outer lateral surface 26 is curved to define a continuous surface that connects the outer posterior surface 20 and the outer anterior surface 16. Likewise, the outer medial surface 30 is curved to define a continuous surface that connects the outer posterior surface 20 and the outer anterior surface 16. The outer anterior surface 16 is slightly curved and the outer posterior surface 20 is a generally planar surface.

Figure 2:
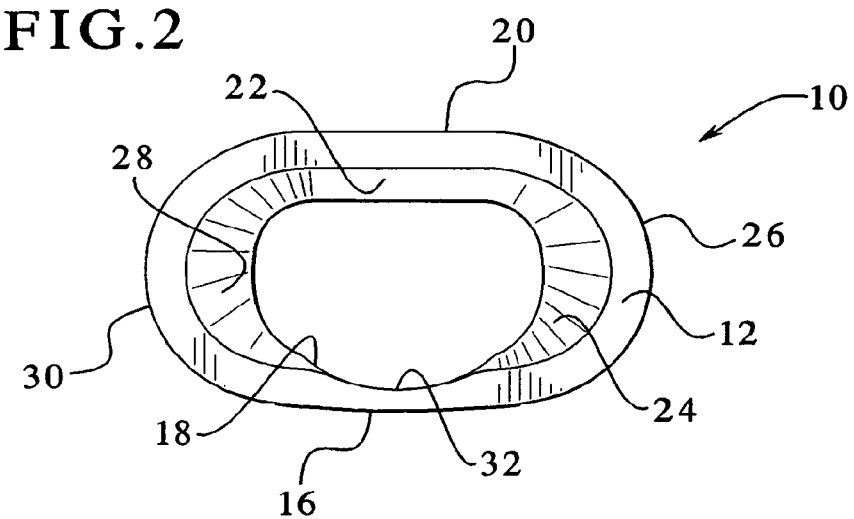
FIG. 2 is a top view of the tibial augment of FIG. 1.
Figure 3:
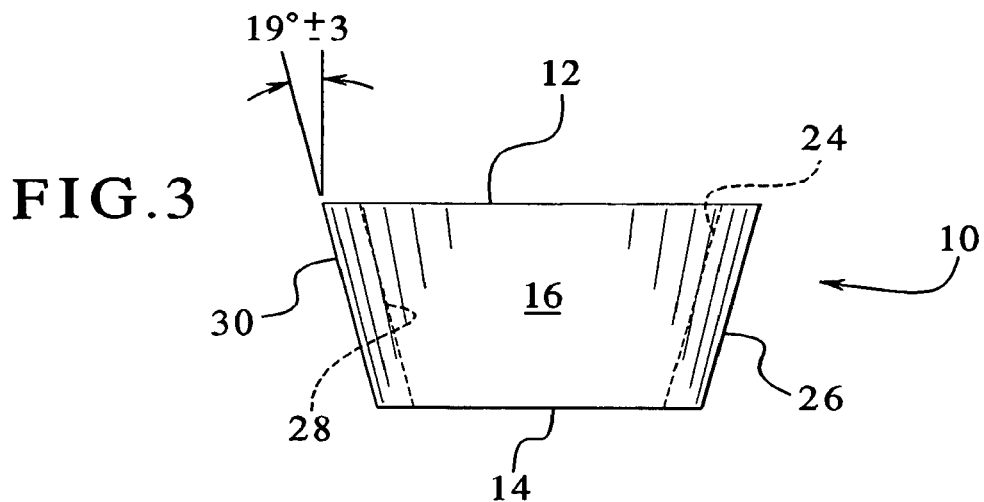
FIG. 3 is an anterior view of the tibial augment of FIG. 1, with the posterior view being identical due to symmetry along the major axis.
Figure 4:
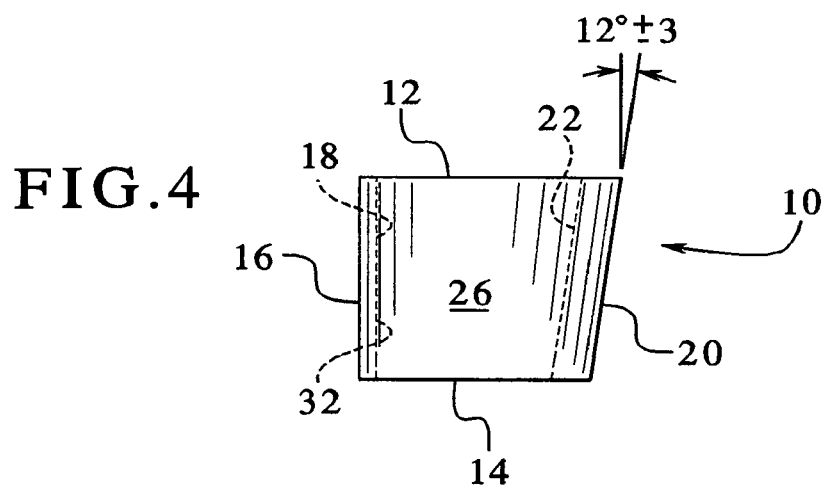
FIG. 4 is a lateral view of the augment of FIG. 1, with the medial view being a mirror image thereof.

As best shown in FIGS. 2 through 4, a majority of the annular member 10 is of a substantially uniform thickness, as most readily depicted by the hidden lines of FIGS. 3 and 4. When an annular member like annular member 10 is made from a metal material that is porous like Trabecular Metal™, it is understood that the porous metal material spans the entirety of this thickness. The major exception to the uniform thickness is a channel 32, shown in FIGS. 1 and 2, which defines a reduced thickness portion. In the preferred embodiment, the thickness of the majority of the augment is preferably approximately 5 mm thick, and the thickness of the reduced thickness portion is preferably approximately 3 mm at its narrowest point. However, other dimensions are also contemplated as being within the scope of the invention.

Although the preferred embodiment includes walls of a substantially uniform thickness, with a reduced thickness portion near channel 32, it is also contemplated that the walls could be tapered, in either direction, between the proximal and distal surfaces.

Figure 8:
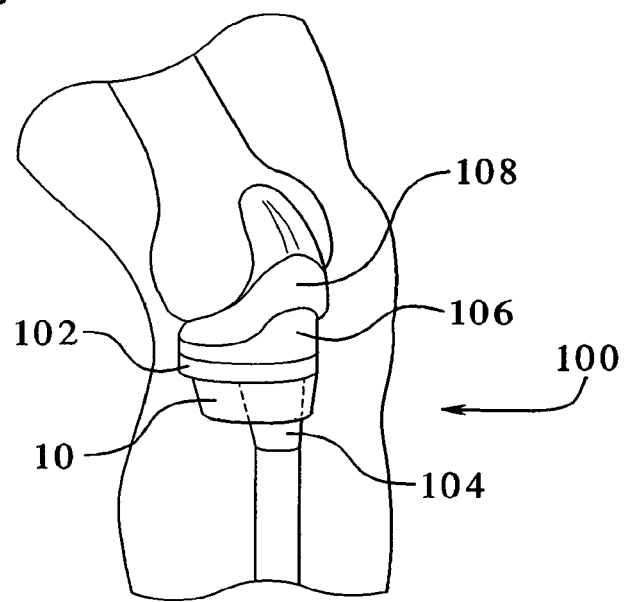
FIG. 8 is a view of a tibial augment of the present invention, shown implanted in place below a knee joint prosthesis.

The reduced thickness portion is preferably included to provide a space for the stem of a stemmed tibial base plate of a knee joint prosthesis. One example of such a stemmed tibial base plate is shown in FIG. 8, which shows a knee joint prosthesis 100 that includes stemmed tibial base plate 102 with a stem 104 extending through the tibial augment 10. FIG. 8 also shows a tibial articulating surface 106 and a femoral component 108, which are also parts of the knee joint prosthesis 100. Although the present augment 10 is shown and described for use with a stemmed tibial base plate and includes a channel for accommodating the base plate's stem, it is contemplated that the present invention could also be used with other forms of base plates without stems, and therefore the channel could be omitted. Further, it is also contemplated that the inner surfaces of the tibial augment of the present invention could be modified to accommodate other designs of tibial base plates, such as pegged base plate designs.

As shown in FIG. 3, both the outer medial surface 30 and the outer lateral surface 26 have a distal taper (i.e. downward slope) of between approximately 8 degrees and approximately 30 degrees, with a taper of approximately 19 degrees being preferred. Such tapers replicate the tapers commonly found in corresponding areas of the proximal portions of human tibias. Since the thickness of the annular member 10 is generally uniform from its proximal side to its distal side, the inner medial surface 28 and the inner lateral surface 24 will also have the same taper as the outer lateral and medial surfaces.

Referring now to FIG. 4, the outer posterior surface 20 has a distal taper of less than approximately 17 degrees, with a taper of approximately 12 degrees being preferred. The outer anterior surface 16 is an essentially normal surface relative to the proximal surface 12. Like the tapers of the lateral and medial surfaces, those of the anterior and posterior surfaces were also chosen to mimic the tapers of the appropriate portions of a human tibia. Once again, due to the relatively uniform thickness, the tapers of the inner posterior and anterior surfaces (22 and 18, respectively) will be the same as those of the corresponding outer posterior and anterior surfaces (20 and 16, respectively).

The present invention also comprises a system of a plurality of differently sized augments that can be held on hand in order to accommodate tibias of different sizes. It is contemplated that three or four different sizes in the anterior/posterior-medial/lateral direction should suffice for most applications. For example, the lateral/medial dimension could range from about 40 mm to about 80 mm, when measured from its widest point (which is at the proximal surface). Thus, if four sizes were to be used, the lateral/medial dimension of the smallest tibial augment (at its widest point) would be 48 mm for an extra small augment, 52 mm for a small augment, 59 mm for a medium augment and 67 mm for a large augment. Additionally, the anterior/posterior dimension could range from about 30 mm to about 40 mm, when measured from the widest point in the anterior/posterior direction (which is at the proximal surface). Thus, the approximate minimum dimensions for extra small, small, medium, and large augments would be 33 mm, 34 mm, 36 m and 38 mm, respectively.

Further two different heights of augments should be available, where the height is measured from the proximal surface 12 to the distal surface 14. In cases where the decay has only extended a small distance into the tibia, a shorter augment can be used than that needed where the decay has extended to a greater depth of the bone. As a general rule, as much healthy bone should be preserved as possible. However, if the decay is relatively deep, two augments of different sizes may be stacked upon each other. For example, a small augment may be stacked upon an extra small augment; a medium augment may be stacked upon a small augment; or a large augment may be stacked upon a medium augment. Due to the shapes of the outer peripheries of the augments, stacking essentially creates extensions of the outer lateral, medial, posterior and anterior surfaces.

Figure 5:
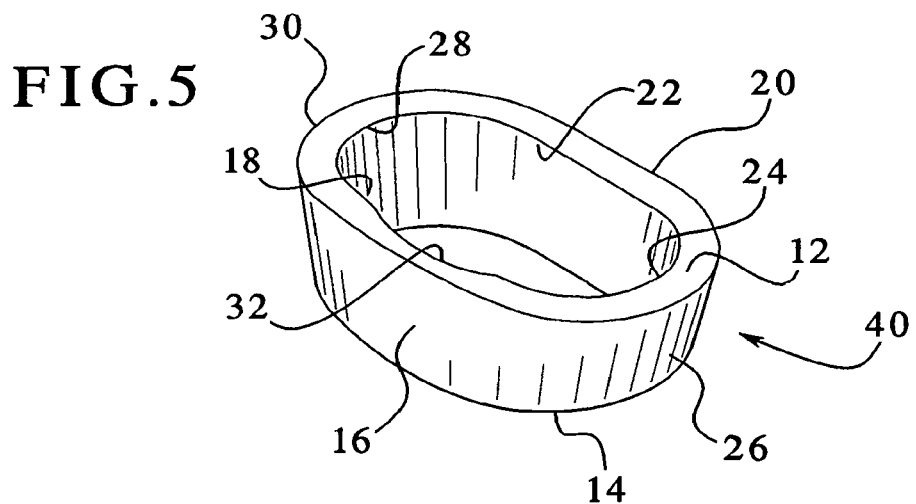
FIG. 5 is a perspective view of a tibial augment of a different height than that shown in the FIG. 1 embodiment.

It is believed that two different heights should be sufficient to remedy most tibial bone decay situations that are suitable for correction by implantation of a tibial augment. For example, augments could be available in 15 mm and 30 mm heights. However, more than two heights may also be produced, if desired. The tibial augment 10 shown in FIGS. 1 through 3 is one example of an augment of the 30 mm height, and the tibial augment 40 shown in FIG. 5 is one example of an augment of the 15 mm height. The augment 40 of FIG. 5 is essentially the same as the augment 10 of FIGS. 1 through 4, except for the height thereof. Accordingly, the same index numbers have been used in FIG. 5 as those used in FIGS. 1 through 4.

In order to accommodate the requirements of most situations, multiple sizes and shapes of augments may be desired. In the preferred embodiment of a set of augments, six different sizes of augment are believed to be sufficient—extra small, small, medium and large in a short height (such as 15 mm) and medium and large in a tall height (such as 30 mm). Thus, in a system including these basic sizes, there is no tall height (such as 30 mm) augments in the extra small size or the small size. It is believed that defective bone portions corresponding to these two sizes are better suited to be corrected by other methods.

Of course, all of the dimensions discussed above (and below) are being provided by way of example only, and other dimensions are also contemplated as being within the scope of the invention. However, the dimensions provided, as divided into four different increments, are believed to be able to accommodate the needs of the majority of patients. Accordingly, only a limited stock of differently sized augments would need to be kept on hand. Thus, for example, a kit of augments would only need to contain four different sizes of augments of the 15 mm height, and two different sizes of augments of the 30 mm height.

Figure 6A:
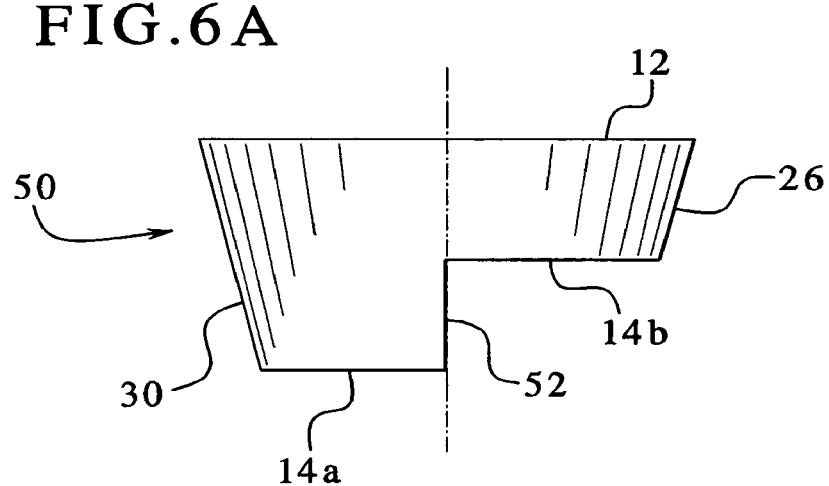
FIGS. 6A-6C are anterior views of three different stepped versions of the tibial augment of the present invention.
Figure 6B:
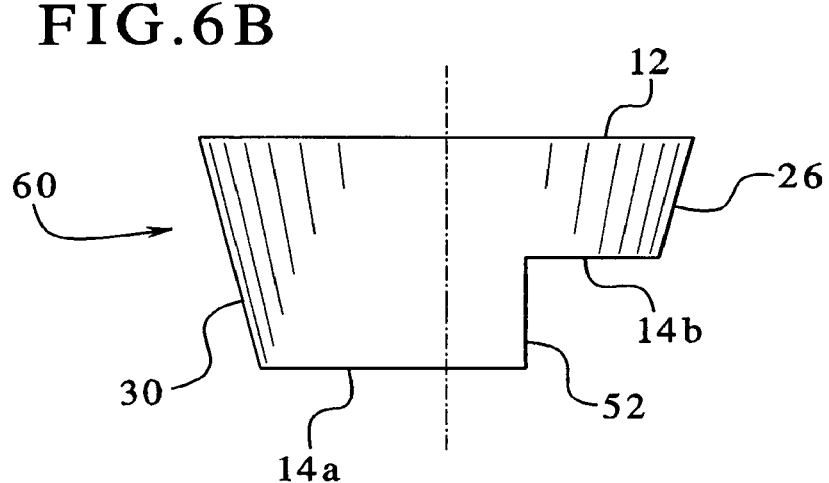
Figure 6C:
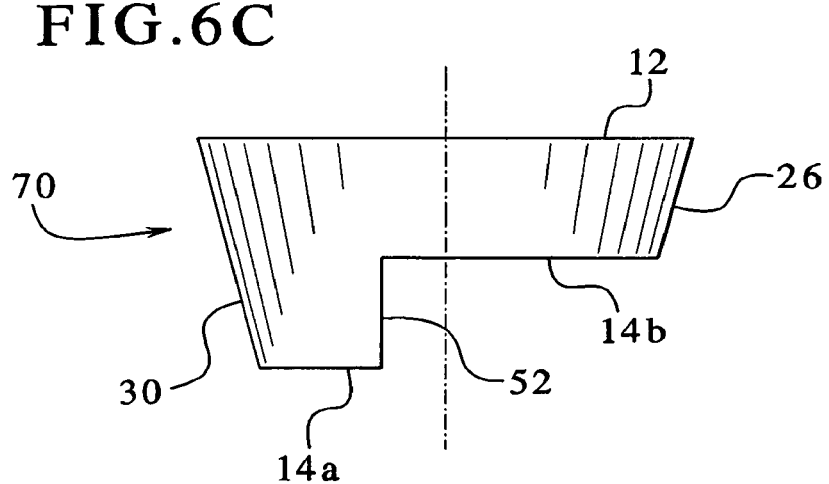

Turning now to FIGS. 6A through 6C, three different stepped versions of a tibial augment are shown. More specifically, FIG. 6A shows stepped augment 50, FIG. 6B shows stepped augment 60 and FIG. 6C shows stepped augment 70. Since only the distal surface of the stepped augments is different from the augment of FIGS. 1 through 4, only that portion needs to be discussed. In addition, the same index numbers as those used in FIGS. 1 through 4 will be used for similar features found in FIGS. 6A through 6C.

FIG. 6A shows tibial augment 50, which includes a stepped distal surface 14a/14b with a transition surface 52 therebetween. As shown in the figure, distal surface 14a is located at a greater distance from the proximal surface 12 than distal surface 14b. In this embodiment, the transition surface 52 is located approximately midway between the outer medial surface 30 and the outer lateral surface 26.

A second embodiment of a stepped tibial augment is shown in FIG. 6B, as represented by tibial augment 60. In this embodiment, as in the FIG. 6A embodiment, distal surface 14a is located at a greater distance from the proximal surface 12 than distal surface 14b. The main difference between this embodiment and the FIG. 6A embodiment is the location of the transition surface 52. In this embodiment, the transition surface 52 is located closer to the outer lateral surface 26 than to the outer medial surface 30.

FIG. 6C shows a third embodiment of a stepped tibial augment 70. In this embodiment, as in the embodiments of FIGS. 6A and 6B, distal surface 14a is located at a greater distance from the proximal surface 12 than distal surface 14b. The main difference between this embodiment and the other two embodiments is the location of the transition surface 52. In this embodiment, the transition surface 52 is located closer to the outer medial surface 30 than to the outer lateral surface 26.

The embodiments of FIGS. 6A through 6C are especially useful where to there has been uneven tibial decay, i.e., where there is more decay on either the lateral side or the medial side than on the other side. By using one of the stepped tibial augments shown in FIGS. 6A through 6C, more healthy bone, if it exists on one side or the other, can be preserved, and mostly only defective bone will end up being removed when forming a stepped cavity to implant the tibial augment. In other words, the base of the cavity into which the stepped tibial augment will be implanted will be stepped to correspond to the stepped distal surface of the augment. Such a stepped-base cavity provides for preservation of more healthy bone on the shallower side, as compared with a flat-based cavity where bone has been removed to a depth equal to the depth of the lowest damaged area of bone.

Suggested heights for the stepped tibial augments of FIGS. 6A through 6C are 15 mm and 30 mm (as measured from the proximal surface 12 to the distal surfaces 14b and 14a, respectively). Of course, other heights are also contemplated as being within the scope of the invention.

Figure 7:
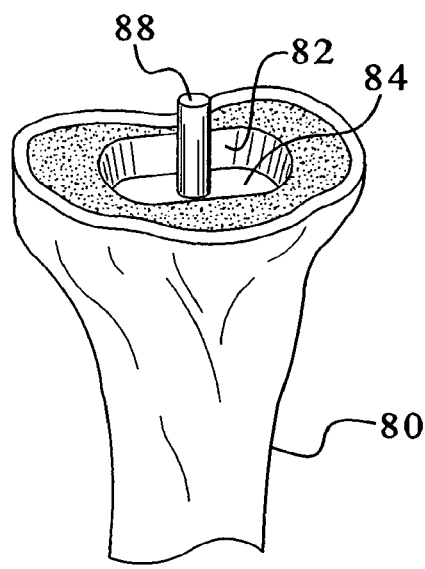
FIG. 7 is a view of a tibia, shown with the damaged proximal bone surface removed and also including a cavity within which a tibial augment of the present invention will be implanted.

FIG. 7 shows an example of a human tibia 80 into which a cavity 82 has been prepared or formed in a proximal portion thereof. The cavity 82 of this example has a flat base 84, so it is suitable for tibial augments with flat distal surfaces, such as those depicted in FIGS. 1 through 5. However, those of ordinary skill in the art should be able to adapt the flat base 84 into a stepped base using the cavity forming techniques described hereinbelow.

The tibia 80 of FIG. 7 is shown in a state prior to implantation of a tibial augment and a knee joint prosthesis. More specifically, the extreme proximal portion of the tibia 80 has been removed. Normally, most, if not all, of the removed proximal portion will be damaged tibial bone. However, a small amount of healthy bone may also need to be removed at the same time in order to provide a relatively flat surface upon which the flat-bottomed tibial base plate 102 (FIG. 8) can be seated.

Either prior to removing the extreme proximal portion 86, or immediately after removing it (depending upon which surgical techniques are used), an intramedullary rod 88 may be inserted and used to define the relationship between the knee prosthesis stem and the tibial augment.

An example of a tibial augment 10 that has been implanted into a human tibia is shown in FIG. 8. This figure shows how the tibial augment 10 that is seated within a cavity, such as cavity 82 of FIG. 7, is positioned directly distal of the stemmed tibial base plate 102. Preferably, the tibial base plate 102 is cemented to the tibial augment 10. The remainder of the components of the knee joint prosthesis 100 (the articulating surface 106, the femoral component 108, etc.) are all implanted in the customary manner. It should be noted that although only one form of knee joint prosthesis has been shown and described, the tibial augments of the present invention can be used with other types of knee joint prostheses.

Figure 9:
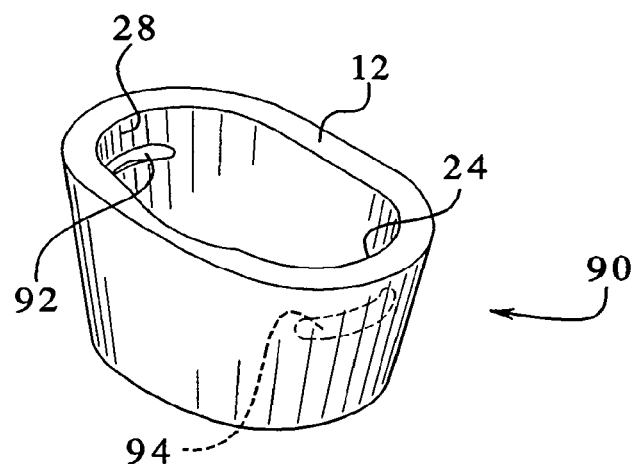
FIG. 9 is a perspective view of a provisional tibial augment of the present invention.

FIG. 9 shows an example of a provisional tibial augment 90, which is a temporary augment used as a test to ensure that the permanent augment will fit properly within the cavity. Although only one size provisional is shown and described, provisional augments should be made to correspond to every size of tibial augment, including the stepped augments. There are two main differences between the provisional augment 90 and the permanent augments of FIGS. 1 through 6C.

First, the provisional augment 90 may be made of a material which indicates the bony areas of the provisional so that the surgeon can visualize how the augment fits within the cavity. For example, the provisional may be made of a transparent or photo-elastic material. One example of a suggested material for the provisional is polyphenylsulfone, although other materials are also contemplated.

Second, provisional augments preferably include a set of grooves 92/94 on the inner medial surface 28 and the inner lateral surface 24. These grooves 92 and 94 extend in the generally lateral/medial direction, and are configured to cooperate with ribs 96 on holder 110 shown in FIG. 10. The holder 110 is designed to facilitate insertion and removal of the provisional augment 90 to/from the cavity 82 (FIG. 7) in order to determine that there is a proper fit between the cavity and the provisional augment (and therefore there is necessarily a proper fit with the permanent augment also, since both the provisional and the permanent augment are the same size and shape).

Figure 10:
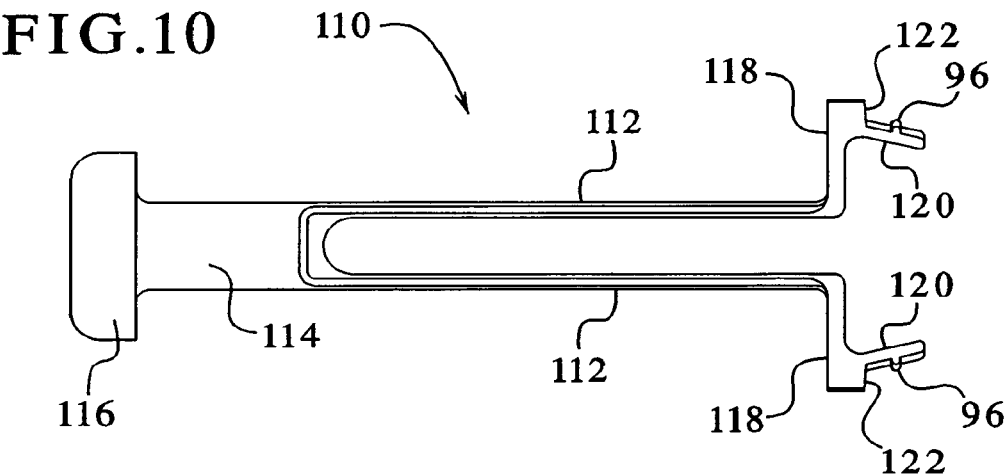
FIG. 10 is a top view of a holder of the present invention, where the holder is intended for use with the provisional of FIG. 9.
Figure 11:
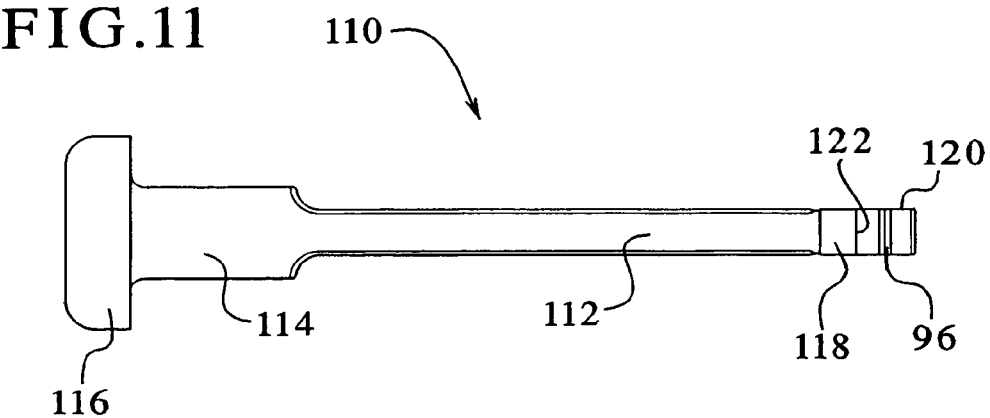
FIG. 11 is a side view of the holder of FIG. 10.
Figure 14:
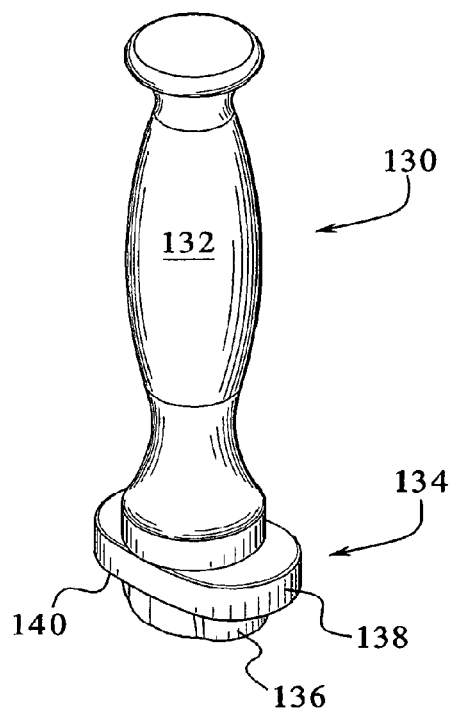
FIG. 14 is a perspective view of a pusher of the present invention, which pusher is intended to be used to implant the tibial augment.
Figure 15:
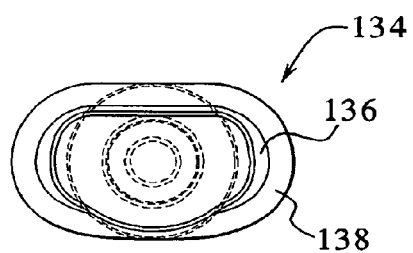
FIG. 15 is a bottom view of the pusher of FIG. 14.

The holder 110 includes two flexible legs 112 that extend in one direction (to the left, as shown in FIGS. 10 and 11) to a body portion 114 that is topped with a crown portion 116. As shown towards the right-hand sides of FIGS. 10 and 11, each leg 112 connects with a shoulder portion 118. Each shoulder portion 118 in turn extends into a finger portion 120, upon which the ribs 96 are situated. The lowermost surfaces of the shoulders 118 each include a stop surface 122, which is used to align the holder 110 with the proximal surface 12 of the provisional 90 (FIG. 9) to facilitate the mating of the ribs 96 of the holder 110 with the grooves 92 and 94 of the provisional 90.

The holder 110 is preferably made of stainless steel, but it is contemplated that it may also be fabricated from plastic. A key consideration when selecting material is that the legs 112 must be flexible enough to be able to be biased inwardly towards each other with light force applied from the surgeon's thumb and forefinger, but they must also be resilient enough to return to their original positions when the force is removed.

In use, the legs 112 of the holder 110 are flexed inwardly by the surgeon, and the fingers 120 are inserted into the interior of the provisional 90 (which is an annular member). Once the stops 122 contact the proximal surface 12 of the provisional, the ribs 96 of the holder should be face to face with the grooves 92 and 94 of the provisional 90. Pressure on the legs 112 can now be released, and the legs 112 will flex outwardly until the ribs 96 mate with the grooves 92 and 94. At this point, the holder 110 can be moved (such as by holding the crown portion 116 and/or by the body portion 114), and the provisional 90 will remain attached to the holder 110, for inserting/removing the provisional 90 to/from the cavity 82 (FIG. 7).

One important feature of the holder 110 is that it can be disengaged from the provisional without affecting the position of the provisional. Thus, once the provisional is seated in the desired position, the legs 112 can be squeezed together, and the holder 110 can be removed without disrupting the position of the provisional.

Only one size holder 110 has been shown, but it should be understood that since the ribs of the holder are specifically configured to make contact with the grooves on the inner surfaces of a provisional tibial augment, a different sized holder is necessary for each different sized provisional. However, since the grooves are near the proximal surface of the each provisional, no additional holder needs to be fabricated for a provisional that has the same sized proximal surface as another provisional. In the preferred set of augments and provisionals, there are six basic sizes—(1) extra small with 15 mm height; (2) small with 15 mm height; (3) medium with 15 mm height; (4) medium with 30 mm height; and (5) large with 15 mm height and (6) large with 30 mm height. However, in the preferred embodiment, the 30 mm height medium-sized provisional (or augment) is essentially a 15 mm height medium-sized provisional (augment) stacked upon a 15 mm height small-sized provisional (augment). Similarly, in the preferred embodiment, the 30 mm height large-sized provisional (or augment) is essentially a 15 mm large-sized provisional (augment) stacked upon a 15 mm medium-sized provisional (augment). Thus, the 30 mm height medium-sized provisional can employ the same holder as the 15 mm medium-sized provisional (since they have the same proximal dimensions), and the 30 mm large-sized provisional can employ the same holder as the 15 mm large-sized provisional. Accordingly, in the preferred set of six differently sized provisionals, only four holders are utilized because one holder does double duty for both the 30 mm medium provisional and the 15 mm medium provisional, and another holder does double duty for both the 30 mm large provisional and the 15 mm large provisional.

Further, if extra small, small, medium and large stepped provisionals are also included, the number of holders does not need to be increased because the rib spacing on a stepped provisional is the same as that of a similarly sized flat-bottomed provisional. Thus, the extra small holder can be used with the extra small stepped provisional, the small holder with the small stepped provisional, the medium holder with the medium stepped provisional, and the large holder with the large stepped provisional.

Turning now to FIGS. 12 and 13, a second embodiment of the holder will be shown and described. The second embodiment of the holder, which will be designated as holder 111, is adjustable so that it can be used with provisionals of a variety of different sizes, as well as with provisionals other than tibial augment provisionals, such as femoral provisionals. Holder 111 includes a body portion 113 that serves as a handle and may optionally include a ribbed surface 115 that allows for a more secure grip. The body portion 113, which defines a longitudinal axis (a vertical axis as shown in FIGS. 12 and 13), is connected to a pair of legs 117. These legs 117 are each preferably L-shaped, and are preferably attached to the lower portion of the body portion 113 by welding (although other attaching means, such as screws, may be used instead). On the other hand, if desired, the legs 117 and the body portion 113 may be formed as a single unit, such as by casting, which will eliminate the need for any attaching means for connecting the legs with the body portion. When viewed together, the body portion 113 and the legs 117 define a generally fork-shaped component, as shown in FIG. 13.

Each of the legs 117 includes a finger 119 connected thereto. The fingers 119 are preferably connected to the legs 117 via an externally threaded shaft 121. The threaded shaft 121 is divided in half such that one half is threaded in one direction and the other half is threaded in the opposite direction. Each of the fingers includes an internally threaded aperture 123 that is configured to mate with the associated portion of the threaded shaft 121. Thus, when knob 125 is turned in one direction, the threaded shaft 121 will rotate within threaded apertures 123, which will cause the fingers 119 to separate from each other, and when the knob is turned in the other direction, the fingers 119 will move towards each other. For example, the threaded shaft 121 could be configured such that clockwise rotation of the knob 125 will cause the fingers 119 to move closer together and counterclockwise rotation will cause the fingers to move farther apart (or, if desired, it could be configured in the opposite manner, where clockwise rotation causes greater separation and counterclockwise rotation reduces the separation distance). As shown in FIG. 13, each of the fingers 119 preferably includes a thickened portion 129, which serves to increase the contact area between the threaded aperture 123 and the threaded shaft 121. Thickened portions 129 also provide stops that prevent the fingers 119 from coming too close together.

For the purpose of connecting the threaded shaft 121 to the legs 117, each of the legs preferably includes an open-ended slot 127 for receiving the ends of the shaft, which are preferably not threaded. After one end of the threaded shaft 121 has been inserted into each slot 127, a small metal block is welded to each slot to close its open-end, which serves to maintain the threaded shaft in position, while still allowing rotation of the threaded shaft with respect to the legs. Of course, other methods of attaching the threaded shaft 121 to the legs 117 are also contemplated as being within the scope of the invention.

A secondary shaft 131 is also provided in parallel with the threaded shaft 121. The secondary shaft 131 is preferably not threaded, and is provided in order to prevent the fingers 119 from rotating with respect to the legs 117 when the threaded shaft 121 is rotated. The fingers 119 are connected to the secondary shaft 131 via a pair of apertures 133 (where one aperture extends through each finger), which allows the fingers to slide along, as well as rotate with respect to, the secondary shaft 131. Optionally, in order to alleviate possible binding as the fingers 119 travel along the secondary shaft 131, the secondary shaft may be slightly tapered from the center thereof. For example, the center portion 135 may be made of full diameter, and extending outwardly therefrom towards the legs 117, the secondary shaft 131 may include a one degree taper (although tapers of different degrees may also be provided), with the ends seated within apertures 133 preferably being of the same diameter as the center portion 135. Preferably, the secondary shaft 131 is welded in place at the apertures 133, although other ways of attaching the secondary shaft to the legs may also be used. Additionally, other means of preventing the fingers 119 from rotating with respect to the threaded shaft are also contemplated as being within the scope of the invention. For example, the legs and/or the body portion may include some form of protrusion extending therefrom for preventing rotation of the fingers 119 with respect to the legs 117, but which still permits the fingers to move sideways (i.e., towards and away from each other) with respect to the legs. As another example, the upper portions of the fingers 119 may be configured to include forks that extend upwardly to straddle the legs 117 and/or the lower portion of the body portion 113.

Each of the fingers 119 also includes a rib 137, and they also each preferably include a stop surface 139. As with holder 110 of FIGS. 10 and 11, the ribs 137 of holder 111 are configured to mate with the grooves 92 and 94 of the provisional 90 (FIG. 9) for inserting and removing the provisional to/from the cavity, and the stop surfaces 139 are used to align the holder 111 with the proximal surface 12 of the provisional 90 to facilitate mating the ribs of the holder with the grooves of the provisional.

The holder 111 is preferably made of stainless steel or of another metal, but other materials may be used for all or for only some of the components. For example, plastic may be used for certain parts such as the body portion 113, the knob 125 and the secondary shaft 131, while a metal or other different material may be used for the remaining components.

In order to accommodate many different sizes of tibial augment provisionals, as well other types of provisionals (such as femoral provisionals), the spacing of the fingers 119 should be able to be adjusted so that the fingers are far enough apart to enable the ribs 137 to engage with the grooves of the largest provisional, as well as to be adjusted to be close enough together for use with the smallest provisional. For example, a distance of approximately two inches between the outer surfaces of the fingers 119 when separated at the maximum distance and a distance of approximately three quarters of an inch when separated at the minimum distance should be sufficient for most uses. Of course, these dimensions are only provided as a suggestion, and other dimensions may also be used.

In use, the knob 125 is rotated to separate the fingers 119 by a distance that is less than the distance that separates the grooves of the provisional being acted upon (such as grooves 92 and 94 of provisional 90 in FIG. 9). The stop surface 139 is positioned upon the proximal surface of the provisional, and the ribs 137 of the holder are aligned with the grooves 92 and 94 of the provisional 90 (FIG. 9). The knob 125 is again rotated to make the ribs 137 engage the grooves 92 and 92, and the provisional 90 is inserted into the cavity 82 (FIG. 7). The holder 111 can be disengaged from the provisional 90 by rotating the knob 125 to bring the fingers 119 closer together, separating the ribs 137 from the grooves 92 and 94. One important feature of the holder 111 is that is allows the ribs to be disengaged from the grooves without significantly altering the location of the provisional within the cavity. When the provisional 90 is to be removed from the cavity 82, the holder 111 is again used in the manner described above.

The preferred embodiments of the provisional and holder combination have been shown and described with grooves on the inner lateral and medial surfaces. However, it is also contemplated that the grooves could be placed on the inner anterior and posterior surfaces, and that the spacing of the fingers on the holder could be adjusted accordingly. Further, detents could be substituted for the grooves, and a spring loaded holder for mating with the detents could also be used.

It is also contemplated that other means for inserting the provisional may also be used. For example, the provisional may include a threaded circular holder into which a threaded handle member can be inserted and removed.

Turning now to FIGS. 14 through 17, these figures show an example of a tibial augment pusher 130, which is used to seat a tibial augment within the cavity of the proximal portion of the tibia. The pusher 130 (or one of the holders) may also be used in conjunction with the provisional tibial augment as a tamp. In situations where a bone graft is necessary to fill a void within the tibia in preparation for receiving the provisional tibial augment within the cavity, the void could be filled with morselized bone and the provisional tibial augment (in combination with a holder or pusher) could be used to tamp the morselized bone into place.

The pusher 130 includes a handle portion 132 and an augment seating portion 134. The augment seating portion 134 is further divided into a head portion 136 and a platform portion 138. The head portion 136 is preferably shaped to mimic the interior surfaces of the tibial augment 10 (FIG. 1), except the head portion 136 is slightly smaller than the corresponding surfaces of the tibial augment 10 associated therewith, which permits the head portion 136 to be easily seated within (and easily withdrawn from) the tibial augment 10. More specifically, there is preferably approximately 0.030 inches (0.762 mm) clearance between the outer surface of the head portion 136 and the inner surfaces of the tibial augment 10, as represented by distance "X" in FIG. 17, which includes (in the main view) a front view of pusher 130 and a magnified view of part of the head portion 136 of the same pusher, but with a tibial augment 10 seated thereon. That is, the magnified view of FIG. 17 shows the head portion 136 in hidden lines to represent that the head portion is hidden behind the augment 10, with the inner surface of the augment (also in hidden lines) spaced from the outer surface of the head portion 136 by distance "X."

Figure 16:
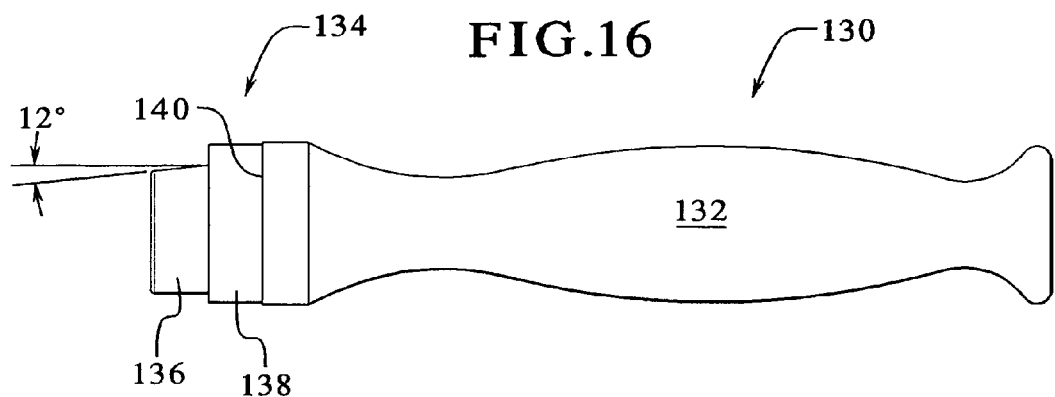
FIG. 16 is a side view of the pusher of FIG. 14.
Figure 17:
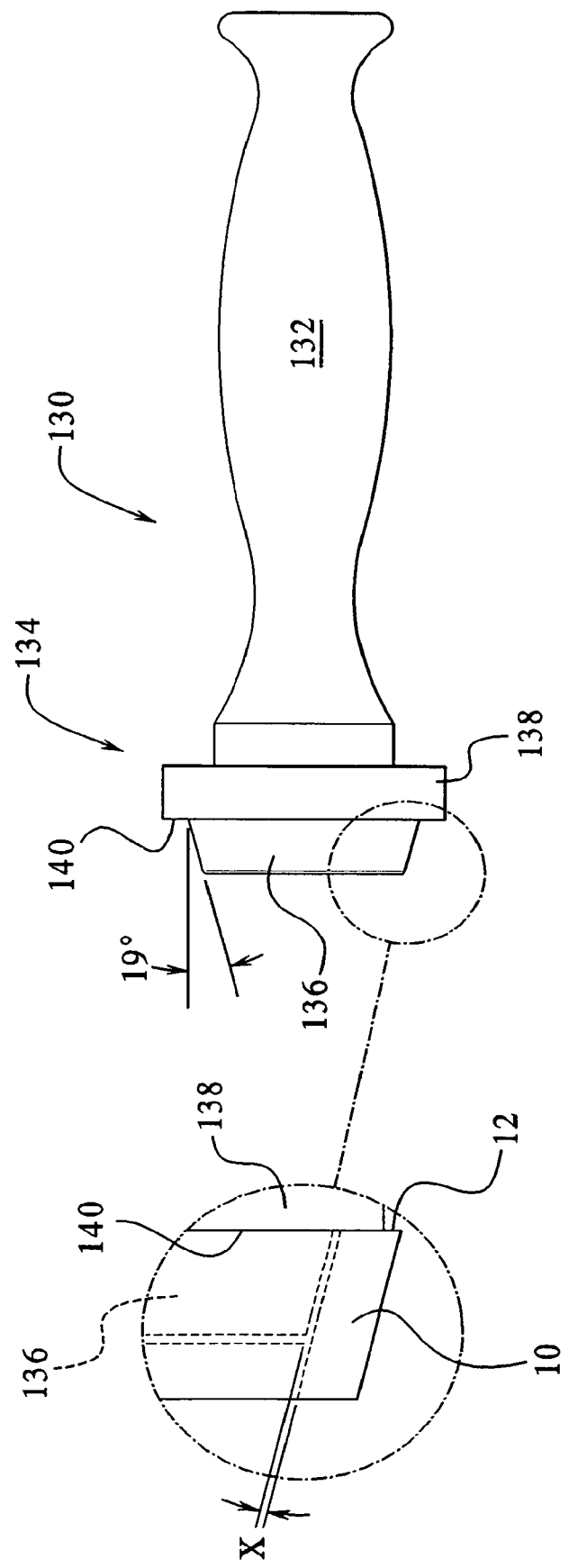
FIG. 17 is a front view of the pusher of FIG. 14, and an enlarged view of the augment seating portion upon which a tibial augment has been seated.

As also shown in the magnified portion of FIG. 17, the proximal surface 12 of the augment 10 contacts the planar surface 140 of the platform portion 138, which provides a surface from which the surgeon can apply light pressure to the augment 10 to align, locate, and to seat it within the cavity 82 (FIG. 7). As can be seen in FIGS. 16 and 17, the planar surface 140 is provided upon the platform portion 138 at the interface between the platform portion 138 and the head portion 136.

Since the shape of the head portion 136 mimics the shape of the interior surfaces of the augment 10, it follows that the head portion 136 should have a taper of approximately 19 degrees (+/−3 degrees) at the surface that corresponds to the inner medial and lateral surfaces (as shown in FIG. 17), and that it should have a taper of approximately 12 degrees (+/−3 degrees) at the surface that corresponds to the inner posterior surface (as shown in FIG. 16). Further, as also shown in FIG. 16, the surface of the head portion 136 that corresponds to the inner anterior surface is not tapered, but is instead substantially perpendicular to the platform portion 138.

In order to properly orient a tibial augment 10 within a cavity, the pusher 130 must have a head portion 136 that is appropriately shaped, as discussed above, and the head portion must also be appropriately sized. Thus, as with the provisional holders 110 discussed earlier, a number of pushers may be provided for the set of augments. For example, if there are four sizes of augments (extra small, small, medium and large), with two heights available (15 mm and 30 mm) for the medium and the large sizes only, then there is a total of six differently sized augments. Accordingly, as with the provisional holders 110, there should also be four differently sized pushers—one pusher for the 15 mm extra small augment; one for the 15 mm small augment; one for the 15 mm medium augment, the 30 mm medium augment, and the medium stepped augments; and one for the 15 large augment, the 30 mm large augment, and the large stepped augments.

In its preferred form, each pusher 130 is preferably made with an aluminum handle portion 132 and an acetyl seating portion 134. However, other materials can also be used. For example, the seating portion could be made from various polymers or metals and the handle portion could be made of a different metal or from plastic.

Turning now to FIGS. 18 through 28, a guide and several associated osteotomes that are all used to create a cavity in the tibia are shown and will be described next. One important aspect of the present invention is that the cavity formed in the tibia (such as cavity 82 of FIG. 7) must be carefully created so that the tibial augment fits as precisely as possible. Among the advantages of a precise fit is that the more precise the fit, the greater the stability of the implant. Accordingly, the present invention includes tools and a method of creating a cavity of the proper size and shape. Although only one method of creating the cavity will be shown and described, other methods may also be used as a supplement to or in place of the method described. For example, a rasp technique may be used to either create the cavity or to make fine adjustments to a cavity created by another method. With such a technique, a rasp shaped like a tibial augment (with a rasp-like outer surface and a handle) is used to remove the bone and form the cavity (or to make fine adjustments to the shape of the cavity).

Figure 18:
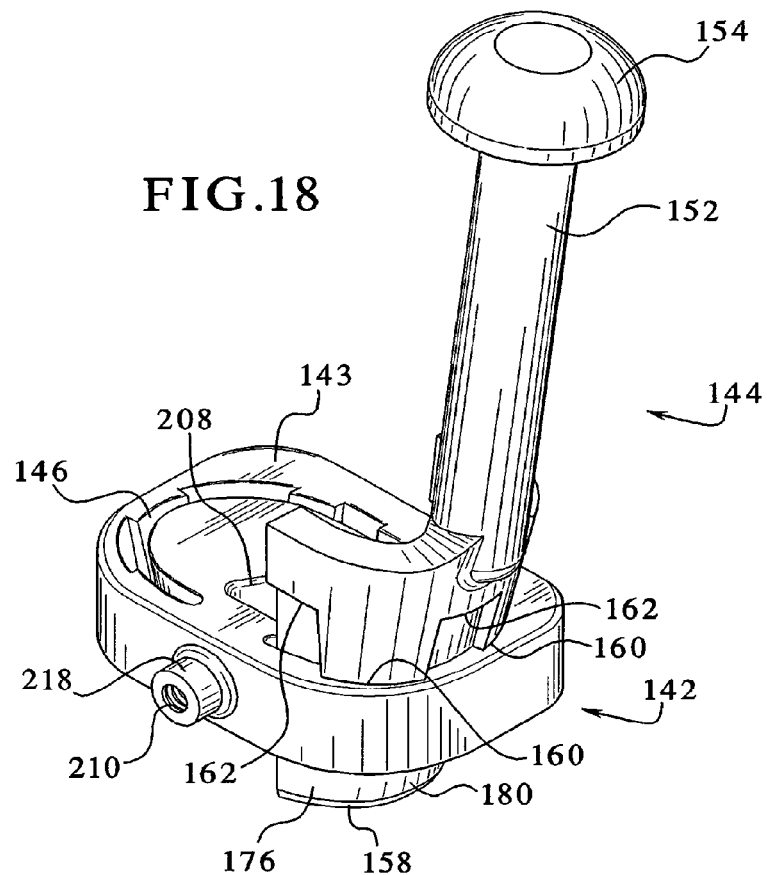
FIG. 18 is a perspective view of a guide and a curved osteotome of the present invention, which are used for making a cavity for the augment.

FIG. 18 shows a preferred embodiment of a guide 142 with a first curved osteotome 144 inserted into a portion of a slot 146 formed within the guide 142. FIG. 25 shows a second curved osteotome 148 (inserted into the guide 142), and FIG. 26 shows a straight osteotome 150 (also inserted into the guide 142). As the following description will show, all three different osteotomes (144, 148 and 150) are required to form the cavity 82 (FIG. 7) because of the configuration of the slot 146, which is specifically configured to properly orient the osteotomes to create a cavity that corresponds to the tibial augment being implanted therein. The osteotomes 144, 148 and 150 are preferably made of stainless steel, although other materials are also contemplated.

As with several of the other components, the osteotomes and guides are preferably configured in a variety of different sizes. In the preferred embodiment, there are four sets of osteotomes (extra small, small, medium and large) and four guides (extra small, small, medium, and large). As described more fully below, these four sets of osteotomes and four guides can be used to create a cavity in the tibia for any of the 15 mm, 30 mm or stepped augments of the preferred embodiment.

Figure 21:
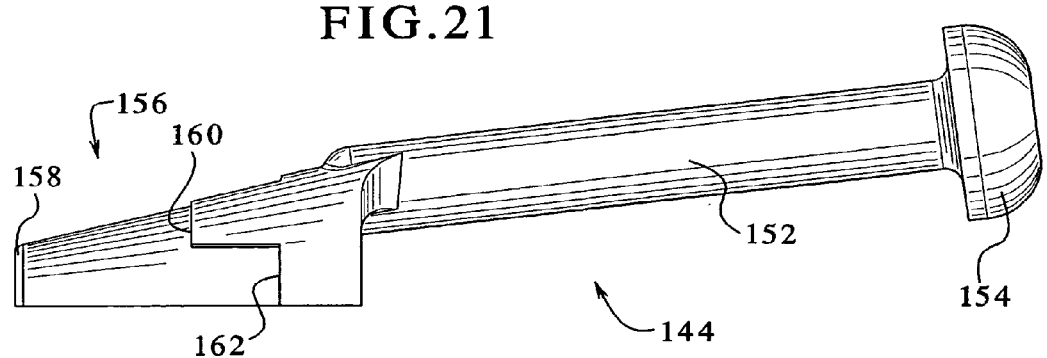
FIG. 21 is a side view of the osteotome of FIG. 18.
Figure 22:
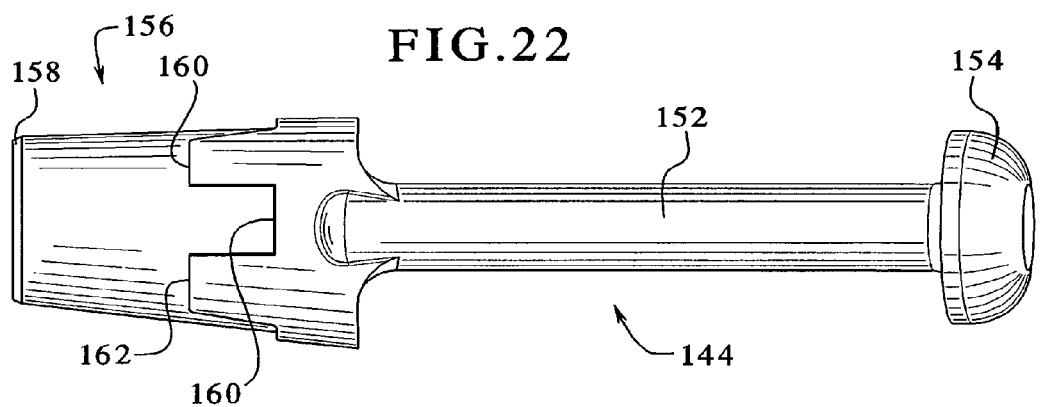
FIG. 22 is a rear view of the osteotome of FIG. 18.

Turning first to FIGS. 18, 21 and 22, the first curved osteotome 144 includes a handle 152 with a crown 154 at the top end thereof. The curved osteotome 144 also includes a cutting portion 156 attached to the handle 152, and the cutting portion includes a tapered edge 158 at its far end and a plurality of first (or distal) stops 160 for hindering the cutting portion from extending into the slot 146 of the guide 142 past a predetermined distance. The cutting portion 156 of the osteotome 144 also includes at least one second (or proximal) stop 162. As described more fully below, the slot 146 in the guide 142 preferably includes a plurality of cutouts 147 (FIG. 19), which allow the distal stops 160 to pass through in order to use the proximal stop 162.

The proximal stop 162 is placed at a greater distance from the tapered edge 158 than the distal stops 160, as can be seen in FIGS. 21 and 22. The use of such staggered stops allows a single osteotome to be used to make two different cavities of two different depths, depending upon which stop is used and also depending upon which size guide is used. Thus, for example, assuming that tibial augments are provided in two different heights (such as 15 mm and 30 mm), accommodations must be made to provide cavities of two different depths (15 mm and 30 mm) so that the depth of the cavity coincides with the height of the tibial augment being placed therein. When a shallow cavity is needed, the set of osteotomes is inserted into the same sized guide (e.g., the set of small osteotomes is used with the small guide, etc.) whereby the exterior stops 160 contact a planar top surface 143 of the guide, hindering the cutting portion 156 from extending further into the guide, and accordingly hindering further extension into the bone. By inserting the set of osteotomes into the same sized guide, distal stops 160 do not mate with cutouts 147, and therefore stops 160 do not pass through cutouts 147. On the other hand, if a deep cavity is needed, the same set of osteotomes are inserted into the incrementally larger guide (e.g. the small osteotomes are used with the medium guide), whereby the distal stops 160 pass through cutouts 147 and the proximal stop 162 contacts the planar top surface 143 of the guide, hindering the cutting portion 156 from extending further into the guide, and accordingly hindering further extension into the bone. The distal and proximal stops of the other osteotomes function in a similar manner. Although in the examples provided the distal and proximal stops have been shown and described as being on the radially exterior sides of the osteotomes, some or all of the stops may be provided on the radially interior sides of the osteotomes. Of course, if all stops are provided on the radially interior sides of the osteotomes, then the cutouts 147 on the guide 142 would have to be changed to be on the radially interior side of the slot 146. Additionally, if the distal stops are provided on the radially exterior side of the osteotome and the proximal stops are provided on the radially interior side (or vice versa), then the cutouts 17 could be omitted, if desired, as long as the slot was made wide enough to accept the cutting portion 156 including the stops.

As mentioned above, FIG. 25 shows an example of a second curved osteotome 148. The second curved osteotome 148 is very similar to the first curved osteotome 144 in that it also includes a handle 164, a crown 166, and a cutting portion 168 with a tapered edge 170 and a plurality of distal stops 172, as well as at least one proximal stop 174.

Figure 23:
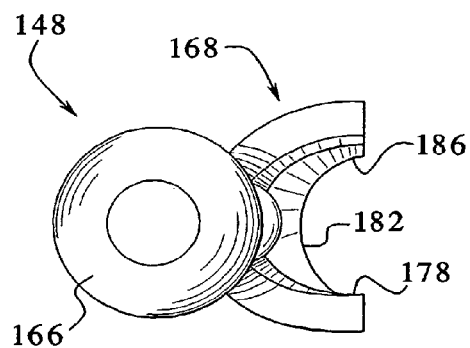
FIG. 23 is a bottom view of the osteotome of FIG. 18.
Figure 24:
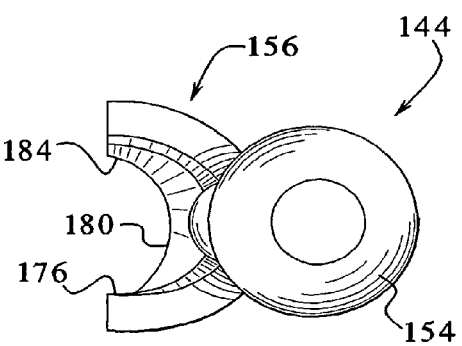
FIG. 24 is a bottom view of the osteotome of FIG. 25.

Although it appears as though the first curved osteotome 144 and the second curved osteotome 148 are identical to each other, but are just shown in different orientations, in actuality, they are mirror images of each other. More specifically, the front cutting area 176 of the first curved osteotome 144 and the front cutting area 178 of the second curved osteotome 148 each have no inclination, which corresponds to the outer anterior surface 16 of the tibial augment 10 (FIG. 4) that also has no incline. Similarly, since the outer posterior surface 20 preferably has an incline of approximately 12 degrees (although inclines within the range of between about 0 to about 17 degrees may also be used), as shown in FIG. 4, the posterior cutting area 184 of the first curved osteotome 144 and the posterior cutting area 186 of the second curved osteotome 148 is also provided with an incline of 12 degrees (or a corresponding incline within the range of about 0 to about 17 degrees, depending upon the exact degree of incline provided to the anterior surface of the tibial augment). Likewise, the outer medial surface 30 and the outer lateral surface 26 of the tibial augment 10 are preferably inclined at 19 degrees (or within the range of between about 8 to about 30 degrees), as shown in FIG. 3, the side cutting area 180 of first curved osteotome 144 and the side cutting area 182 of second curved osteotome 148 are also inclined at 19 degrees (or at whatever selected angle between 8 and 30 degrees that the outer lateral and outer medial surfaces of the augment are provided at). FIGS. 23 and 24 also show how cutting portion 156 is a mirror image of cutting portion 168. Accordingly, the second curved osteotome 148 is not interchangeable with the first curved osteotome 144.

Figure 27:
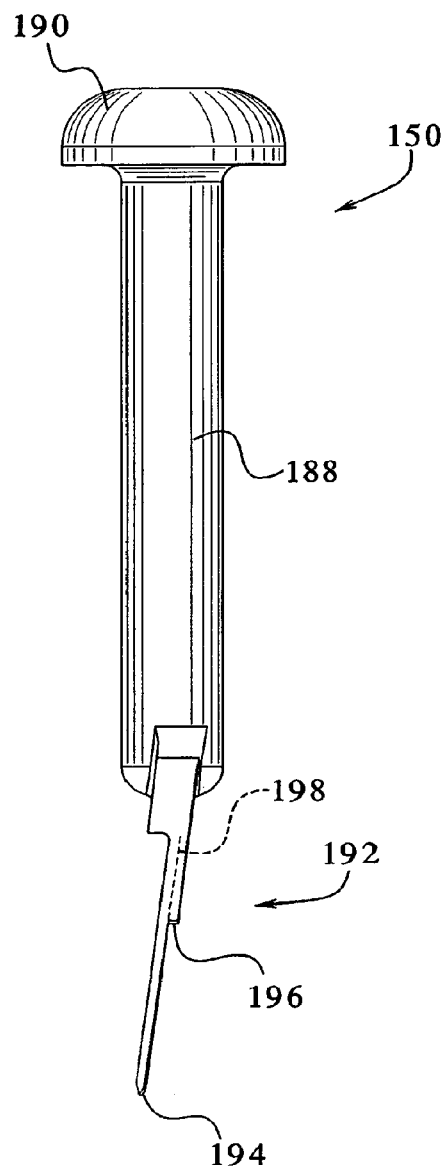
FIG. 27 is a side view of the osteotome of FIG. 26.
Figure 28:
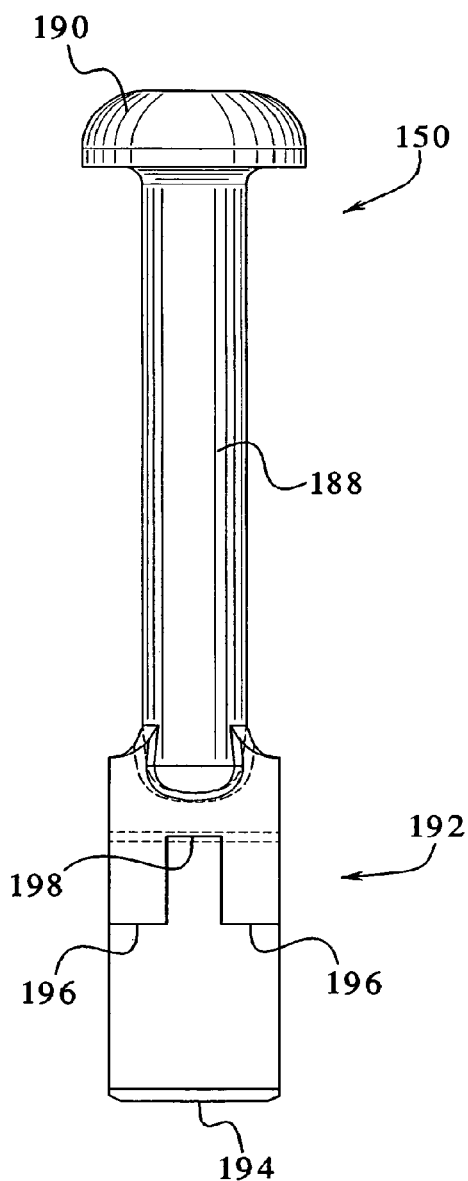
FIG. 28 is a rear view of the osteotome of FIG. 26.

FIGS. 26 through 28 show straight osteotome 150. Like the other osteotomes, the straight osteotome includes a handle 188, a crown 190, and a cutting portion 192 with a tapered edge 194, distal stops 196, and at least one proximal stop 198. As shown in FIG. 27, the cutting portion 192 is preferably inclined with respect to the handle. This degree of incline corresponds to the degree of incline of the outer posterior surface 20 of the tibial augment 10 (FIG. 4). Thus, in the preferred embodiment, there is an incline of approximately 12 degrees. However, inclines of between approximately 0 degrees and approximately 17 degrees are also contemplated as being within the scope of the invention, as well as other degrees of incline. The orientation of the cutting portion 192 with respect to the handle 188 of this osteotome, as well as the other osteotomes, is intended to allow for the proper cutting angle when the handle is held perpendicular to the tibial surface within which the cavity 82 (FIG. 7) has been formed.

Moreover, as shown in FIGS. 18 through 20, 25 and 26, the guide 142 is also provided so that the proper cutting orientation of the osteotomes is maintained, which thereby aids in making a cavity with sidewalls of inclines that correspond to the inclines on the outer surfaces of the tibial augment. As mentioned earlier, the guide 142 includes a slot 146 for guiding the cutting portions (156, 168, 192) of the osteotomes (144, 148, 150). Each portion of the slot 146 is made with a particular incline that matches the incline of the corresponding outer surface of the tibial augment associated therewith. Thus, for example, as shown in hidden lines in FIG. 18, the slot's lateral portion 200 and the slot's medial portion 202 are inclined, respectively, to match the slopes of the outer lateral surface 26 and the outer medial surface 30 of the tibial augment 10, which in the preferred embodiment is a 19 degree incline. Likewise, the slot's posterior portion 204 and its anterior portion 206 are also configured to correspond of the incline of, respectively, the outer posterior surface 20 and the outer anterior surface 16 of the tibial augment 10. Thus, in the preferred embodiment, the slot's posterior portion 204 will be inclined at approximately 12 degrees and the slot's anterior portion 206 will have no incline.

The guide 142 also includes a securing arrangement that is used to secure the guide to the bone within which the cavity is being formed. The securing arrangement includes an aperture 208 that is configured to receive the intramedullary rod 88 (FIG. 7), which serves as both a reference point for the guide and as the stable member that the guide is secured upon. The securing arrangement also includes a threaded hole 210 (FIG. 18) that is configured to receive a setscrew 212 (FIG. 19), which is comprised of a head 214 and a threaded shaft 216. Alternately, the setscrew could also be replaced with a thumbscrew or the head could be replaced with a lever or small handle to facilitate tightening without the need for a screwdriver. The threaded hole 210 is preferably made within a collar 218, which allows for additional length of the setscrew 212, and also allows for also easier access to the head of the setscrew, which may be necessary, especially if a thumbscrew of other similar component is used in place of the setscrew.

Figure 19:
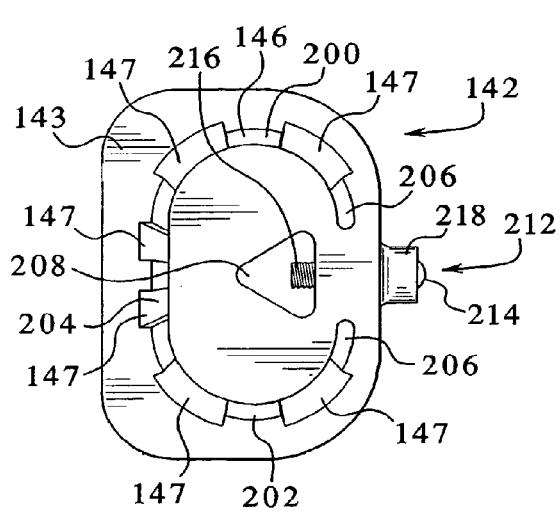
FIG. 19 is a bottom view of the guide of FIG. 18.
Figure 20:
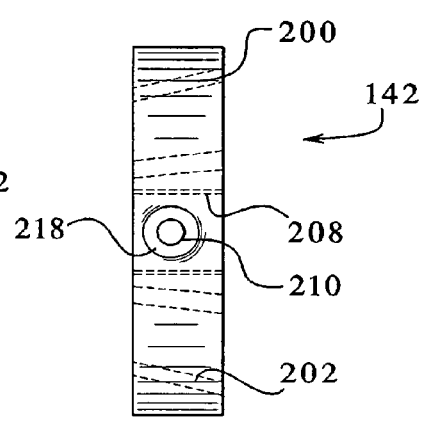
FIG. 20 is a side view of the guide of FIG. 18.

The slot 146 of the guide 142 is not annular, but instead includes a gap near its anterior portion 206, as best shown in FIG. 19. This gap is where the threaded shaft 216 of the setscrew extends through the guide. If this gap in the slot 146 were not present, there is a chance that the threaded shaft 216 of the setscrew could accidentally be damaged if an osteotome were inserted into the slot at this area. Damaging the setscrew could result in misalignment of the guide with respect to the bone, or it could make it difficult to remove the guide from the intramedullary rod 88.

With regard to sizing, there should be one guide and one set of three osteotomes (two curved and one straight osteotome) for each 15 mm sized tibial augment. Further, additional guides and osteotomes need not be provided for the 30 mm sized or for the stepped augments. Thus, if four sizes of augments (extra small, small, medium and large) are provided, there should be four different sizes of guides and four sets of osteotomes, with three osteotomes in each set, for a total of twelve different osteotomes. To make cavities for any of the 15 mm augments, the same sized set of osteotomes and guide are used. For example, to make a cavity for a 15 mm extra small augment, the extra small set of osteotomes and the extra small guide is used. However, to make a cavity for one of the 30 mm augments, the same sized guide is used, but the set of osteotomes for the next smaller size is used. For example, to make a cavity for a 30 mm medium augment, the medium guide is used along with the small set of osteotomes. In other words, no matter what depth cavity is being created (15 mm or 30 mm), the guide that is the same size as the augment being inserted (extra small, small, medium or large) will always be used. However, when 30 mm depth cavities are being created, the set of osteotomes of one size smaller than the augment are used, otherwise (for 15 mm depth cavities), the set of osteotomes of the same size as the augment are used.

To further clarify this point, the following specific examples are provided. Assume that one intends to prepare a cavity suitable for the medium sized augment (of either 15 mm height or 30 mm height). First, for either case (15 mm or 30 mm), the medium sized guide 142 is affixed to the intramedullary rod 88. For creating a 15 mm depth cavity for the medium augment, medium osteotome 144 is inserted into the correspondingly sized medium guide, whereby the distal stop 160 contacts the planar top surface 143 of the guide, hindering the cutting portion 156 from extending further into the guide, past the desired 15 mm depth. The other medium osteotomes are also used in the same manner, with the stops operating in a similar manner to create a 15 mm depth cavity for the 15 mm medium augment.

To create a 30 mm depth cavity for the 30 mm medium augment, the set of small osteotomes (i.e., the osteotomes of one incremental size smaller than the augment) would be inserted into the appropriate position of the slot 146, instead of using the medium osteotomes discussed above. When small osteotome 144 is appropriately inserted into the incrementally larger medium guide, the distal stop 160 passes through the medium guide cutout 147, allowing the cutting portion 156 of the osteotome to extend further into the bone until the proximal stop 162 contacts the planar top surface 143 of the guide. The contact of the proximal stop 162 with the top planar surface hinders the cutting portion from extending further into the guide than the desired 30 mm, and accordingly hinders further extension into the bone. (On the other hand, if small osteotome 144 is inserted into the correspondingly sized small guide, the distal stop 160 contacts the planar top surface 143 of the guide, hindering the cutting portion of the 156 from extending further into the guide so that a 15 mm deep cavity can be created). The distal and proximal stops of the other small osteotomes function in a similar manner, and a 30 mm depth cavity for the medium augment is created by using all three small osteotomes with the medium guide.

To form a cavity in the proximal portion of the tibia, an appropriately sized guide 142 and an appropriately sized set of osteotomes are selected. After the intramedullary rod 88 (FIG. 7) has been implanted within the tibia 80, the aperture 208 of the guide 142 is slid over the intramedullary rod 88, and the guide 142 is secured in place by tightening the setscrew 212. It should be noted that the aperture 208 is preferably triangular, as best shown in FIG. 19, which allows for the intramedullary rod 88 to have an increasingly secure fit as the setscrew is tightened because of the way the rod is seated at the apex of the triangle.

Once the guide 142 is securely attached to intramedullary rod 88, one of the appropriately sized osteotomes, such as the first curved osteotome 144, is inserted into the appropriate position of the slot 146. More specifically, the first curved osteotome 144 is inserted into portion 200 of the slot 146. It should be noted that the osteotomes may be used in any desired order.

As discussed above, the desired depth of cavity is formed by using the appropriate combination of a particularly sized set of osteotomes with an appropriately sized guide, whereby either proximal stops 198 or distal stops 196 are utilized to result in a cut of an appropriate depth. Also, if one of the stepped tibial augments shown in FIGS. 6A through 6C is intended to be implanted, cuts of one depth may be made at one area of the cavity and cuts of another depth may be made at another area in order to form an appropriate cavity with a stepped bottom to accommodate the stepped distal surface 14a/14b of FIGS. 6A through 6C.

Next, one of the other osteotomes, such as the straight osteotome 150 (FIGS. 26-28), is inserted into the appropriate portion of the slot. As shown in FIG. 26, the straight osteotome 150 is inserted into the slot's posterior portion 204 (best seen in FIG. 19). As described above, the appropriate stop, or stops, (either proximal stop 198 or distal stops 196) is/are utilized to result in a cut of the appropriate depth.

Finally, the remaining osteotome, which in this case is the second curved osteotome 148 (FIG. 25), is inserted into the appropriate portion of the slot 146, which in this case is the medial portion 202 (FIG. 19). As with the other osteotomes, the appropriate stop, or stops, (either proximal stop 174 or distal stops 172) is/are utilized to result in a cut of the appropriate depth. After all three osteotomes have been used, the guide 142 may be removed from the intramedullary rod 80 by loosening the setscrew 218 and sliding the guide upwardly and off of the intramedullary rod. At this point, the bone to be removed should be cut to the desired depth, and it merely needs to be taken from the site to form the cavity 82 (FIG. 7). If necessary, an additional cut may need to be made with the straight osteotome 150, or one of the other osteotomes, at the area below the gap in the slot 146, between the two edges of the anterior portion 206 (FIG. 19). However, the decayed bone at that area may simply fall from the peripheral bone without requiring an additional cut. Once the bone is completely removed from within the cut area formed by the osteotomes, a cavity that corresponds to the tibial augment being inserted therein should result.

After forming the cavity, which alternatively could be formed using the rasp technique mentioned earlier, as well as by other known techniques, the provisional augment 90 (FIG. 9) may be temporarily implanted to determine whether the cavity is properly sized, or if additional bone needs to be removed. The provisional may be inserted either with the aid of one of the holders 110 or 111 (FIGS. 10 and 12) or by using one of the pushers 130 (FIG. 14), or with a combination of both a holder and a pusher. At this point, the provisional 90 may also be used to trial the locations of the tibial base plate provisionals (or the provisionals of the tibial tray and stem). After the fit is adequately tested with the provisional 90, it can be removed by using the provisional holder 110 or 111 in the manner previously described. Then, the permanent tibial augment, such as augment 10 of FIG. 1, is inserted using the pusher 130 (FIG. 12). After properly seating the augment within the cavity, cement is applied to the proximal surface 12 of the augment, and the stemmed tibial base plate 102 (FIG. 8) is attached to the augment and to the peripheral bone remaining around the cavity. Then, the remainder of the knee joint prosthesis 100 is attached using any desired method, and the surgical procedure continues in the customary manner.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A tibial augment system for a knee joint including a tibia, the system configured to articulate in conjunction with a condyle portion of a femoral component, the system comprising:
   a tibial implant comprising a tibial plate and a tibial stem component extending from said tibial plate; and
   a tibial augment comprising an annular body formed with a porous metal material for facilitating bony ingrowth into said annular body, said annular body including an interior wall and an exterior wall with a thickness of the annular body extending between said interior wall and said exterior wall such that said porous metal material spans the entirety of said thickness, said annular body sized for implantation in the tibia and having an anterior/posterior dimension and a medial/lateral dimension, said interior wall of said annular body providing a passageway that extends entirely through the annular body for accepting said tibial stem component when said annular body is positioned about said tibial stem component.

2. The tibial augment system of claim 1, wherein both the exterior and interior walls have a distal taper where both the exterior and interior walls have a same taper.

3. The tibial augment system of claim 1, wherein the interior wall includes an anterior surface including a channel extending from a proximal end to a distal end of the annular body.

4. The tibial augment system of claim 1, wherein said annular body includes a proximal end and a distal end, the annular body including a medial height between the proximal end and the distal end at a medial most point of the annular body, the annular body including a lateral height between the proximal end and the distal end at a lateral most point of the annular body, the distal end including a stepped surface in which the medial height is nonequal to the lateral height.

5. The tibial augment of claim 1, wherein the annular body is formed with a tantalum based porous material.

6. The tibial augment system of claim 1, wherein said porous metal material provides a highly porous exterior surface to said annular body for facilitating bony ingrowth into said highly porous exterior surface when said annular body is implanted in the tibia.

7. The tibial augment system of claim 1, wherein said annular body includes a proximal end and a distal end, the annular body tapering from the proximal end to the distal end.

8. The tibial augment system of claim 1, wherein a majority of said thickness is approximately 5 mm.

9. The tibial augment system of claim 8, wherein said annular body includes a reduced thickness portion, said reduced thickness portion being approximately 3 mm.

10. The tibial augment system of claim 1, wherein said annular body includes a proximal end and a distal end, said proximal end having a medial-lateral width greater than a medial-lateral width of said distal end.

11. The tibial augment system of claim 1, wherein said annular body includes a proximal end and a distal end, said proximal end having an anterior-posterior width greater than an anterior-posterior width of said distal end.

12. The tibial augment system of claim 1, wherein said annular body is medially-laterally symmetric.

13. The tibial augment system of claim 1, wherein said exterior wall of said annular body includes tibial augment defines a planar posterior surface.

14. The tibial augment system of claim 1, wherein said exterior wall of said annular body includes a curved anterior surface, a curved medial surface, and a curved lateral surface.

15. The tibial augment system of claim 1, wherein said thickness is annular body of said tibial augment defines a constant thickness between said interior wall and said exterior wall.

16. The tibial augment system of claim 1, wherein a proximal face of said annular body is configured to abut tibial augment abuts a distal face of said tibial plate.

17. The tibial augment system of claim 1, wherein the medial/lateral dimension of the annular body ranges from about 40 mm to about 80 mm at a proximal end of the annular body.

18. The tibial augment system of claim 1, wherein the medial/lateral dimension of the annular body is 48 mm.

19. The tibial augment system of claim 1, wherein the medial/lateral dimension of the annular body is 52 mm.

20. The tibial augment system of claim 1, wherein the medial/lateral dimension of the annular body is 59 mm.

21. The tibial augment system of claim 1, wherein the medial/lateral dimension of the annular body is 67 mm.

22. The tibial augment system of claim 17, wherein the anterior/posterior dimension of the annular body ranges from about 30 mm to about 40 mm at a proximal end of the annular body.

23. The tibial augment system of claim 17, wherein the anterior/posterior dimension of the annular body is 33 mm.

24. The tibial augment system of claim 17, wherein the anterior/posterior dimension of the annular body is 34 mm.

25. The tibial augment system of claim 17, wherein the anterior/posterior dimension of the annular body is 36 mm.

26. The tibial augment system of claim 17, wherein the anterior/posterior dimension of the annular body is 38 mm.

27. The tibial augment system of claim 22, wherein an outer lateral surface and an outer medial surface of the exterior wall of the annular body has a distal taper along at least a portion of a height between a proximal face and a distal face of the annular body, the distal taper between approximately 8 degrees and approximately 30 degrees.

28. The tibial augment system of claim 27, wherein the distal taper is approximately 19 degrees.

29. The tibial augment system of claim 22, wherein an outer posterior surface of the exterior wall of the annular body has a distal taper along at least a portion of a height between a proximal face and a distal face of the annular body, wherein the distal taper is less than approximately 17 degrees.

30. The tibial augment system of claim 29, wherein the distal taper is approximately 12 degrees.

31. A tibial augment system for a knee joint including a tibia, the system configured to articulate in conjunction with a condyle portion of a femoral component, the system comprising:
a tibial implant comprising a tibial plate and a tibial stem component extending from said tibial plate; and
a tibial augment implantable in the tibia and comprising an annular body formed with a porous metal material, said porous metal material providing a porous exterior surface to said tibial augment for facilitating bony ingrowth into said porous exterior surface when said tibial augment is implanted in the tibia, said annular body including an interior wall and an exterior wall with a thickness of the annular body extending between said interior wall and said exterior wall such that said porous metal material spans the entirety of said thickness, said annular body being tapered between a proximal end and a distal end of the annular body, said annular body having an anterior/posterior dimension and a medial/lateral dimension, the medial/lateral dimension ranging from about 40 mm to about 80 mm at a proximal end of the annular body, said interior wall of said annular body providing a passageway that extends entirely through the annular body for accepting said tibial stem component when said annular body is positioned about said tibial stem component.

32. A tibial augment system for a knee joint including a tibia, the system configured to articulate in conjunction with a condyle portion of a femoral component, the system comprising:
a tibial implant comprising a tibial plate and a tibial stem component extending from said tibial plate; and
a tibial augment implantable in the tibia and comprising an annular body formed with a porous metal material, said porous metal material providing a porous exterior surface to said tibial augment for facilitating bony ingrowth into said porous exterior surface when said tibial augment is implanted in the tibia, said annular body including an interior wall and an exterior wall with a thickness of the annular body extending between said interior wall and said exterior wall such that said porous metal material spans the entirety of said thickness, said annular body being tapered between a proximal end and a distal end of the annular body, said annular body having an anterior/posterior dimension and a medial/lateral dimension, the anterior/posterior dimension ranging from about 30 mm to about 40 mm at a proximal end of the annular body, said interior wall of said annular body providing a passageway that extends entirely through the annular body for accepting said tibial stem component when said annular body is positioned about said tibial stem component.

33. A tibial augment system for a knee joint including a tibia, the system configured to articulate in conjunction with a condyle portion of a femoral component, the system comprising:
a tibial implant comprising a tibial plate and a tibial stem component extending from said tibial plate; and
a tibial augment implantable in the tibia and comprising an annular body formed with a porous metal material, said porous metal material providing a porous exterior surface to said tibial augment for facilitating bony ingrowth into said porous exterior surface when said tibial augment is implanted in the tibia, said annular body including an interior wall and an exterior wall with a thickness of the annular body extending between said interior wall and said exterior wall such that said porous metal material spans the entirety of said thickness, said annular body having an anterior/posterior dimension and a medial/lateral dimension, said interior wall of said annular body providing a passageway that extends entirely through the annular body for accepting said tibial stem component when said annular body is positioned about said tibial stem component, with an outer medial surface and an outer lateral surface of the exterior wall having a distal taper along at least a portion of a height between a proximal face and a distal face of the annular body, the distal taper between approximately 8 degrees and approximately 30 degrees.

34. A tibial augment system for a knee joint including a tibia, the system configured to articulate in conjunction with a condyle portion of a femoral component, the system comprising:
a tibial implant comprising a tibial plate and a tibial stem component extending from said tibial plate; and a tibial augment implantable in the tibia and comprising an annular body formed with a porous metal material, said porous metal material providing a porous exterior surface to said tibial augment for facilitating bony ingrowth into said porous exterior surface when said tibial augment is implanted in the tibia, said annular body including an interior wall and an exterior wall with a thickness of the annular body extending between said interior wall and said exterior wall such that said porous metal material spans the entirety of said thickness, said annular body having an anterior/posterior dimension and a media/lateral dimension, said interior wall of said annular body providing a passageway that extends entirely through the annular body for accepting said tibial stem component when said annular body is positioned about said tibial stem component, with an outer posterior surface of the exterior wall having a distal taper along at least a portion of a height between a proximal face and a distal face of the annular body, the distal taper being less than approximately 17 degrees.

* * * * *